(12) United States Patent
Green et al.

(10) Patent No.: US 9,433,557 B2
(45) Date of Patent: Sep. 6, 2016

(54) LOADING SYSTEM FOR AN ENCAPSULATION DEVICE

(75) Inventors: Chad Green, San Diego, CA (US); Laura Martinson, San Diego, CA (US); Val Anthony Bellora, San Diego, CA (US); Richard Alexander Grant, Del Mar, CA (US); Evert Kroon, San Diego, CA (US); Emmanuel Edward Baetge, St. Sulpice (CH)

(73) Assignee: VIACYTE, INC., San Diego, CA (US)

( * ) Notice: Subject to any disclaimer, the term of this patent is extended or adjusted under 35 U.S.C. 154(b) by 115 days.

(21) Appl. No.: 14/000,864

(22) PCT Filed: Feb. 21, 2011

(86) PCT No.: PCT/US2011/025628
§ 371 (c)(1),
(2), (4) Date: Oct. 2, 2013

(87) PCT Pub. No.: WO2012/115619
PCT Pub. Date: Aug. 30, 2012

(65) Prior Publication Data
US 2014/0014226 A1    Jan. 16, 2014

(51) Int. Cl.
*A61J 1/20* (2006.01)
*A61F 2/00* (2006.01)
*C12M 1/00* (2006.01)
*A61F 2/02* (2006.01)

(52) U.S. Cl.
CPC ............... *A61J 1/20* (2013.01); *A61F 2/0095* (2013.01); *A61F 2/022* (2013.01)

(58) Field of Classification Search
CPC .............................. A61K 35/28; C12M 23/48
See application file for complete search history.

(56) References Cited

U.S. PATENT DOCUMENTS

| | | |
|---|---|---|
| 5,011,472 A | 4/1991 | Aebischer |
| 5,284,481 A | 2/1994 | Soika et al. |
| 5,314,471 A | 5/1994 | Brauker et al. |
| 5,368,555 A | 11/1994 | Sussman et al. |
| 5,545,223 A | 8/1996 | Neuenfeldt et al. |
| 5,593,440 A | 1/1997 | Brauker et al. |
| 5,713,888 A | 2/1998 | Neuenfeldt et al. |
| 5,733,336 A | 3/1998 | Neuenfeldt et al. |
| 5,837,444 A * | 11/1998 | Shah .............................. 435/4 |
| 5,964,261 A | 10/1999 | Neuenfeldt et al. |
| 5,976,780 A | 11/1999 | Shah |
| 6,060,640 A | 5/2000 | Pauley et al. |
| 6,620,123 B1 | 9/2003 | Mitragori et al. |
| 6,814,086 B2 | 11/2004 | Stallings |
| 6,887,239 B2 | 5/2005 | Elstrom et al. |
| 7,427,415 B2 | 9/2008 | Scharp et al. |

(Continued)

FOREIGN PATENT DOCUMENTS

| | | |
|---|---|---|
| WO | 2005063971 | 7/2005 |
| WO | 2010129294 A2 | 11/2010 |

(Continued)

*Primary Examiner* — Nathan Bowers
(74) *Attorney, Agent, or Firm* — The Law Office of Jane K. Babin, Professional Corporation; Jane K. Babin

(57) ABSTRACT

The present invention provides, in at least one embodiment, a loading device, system and method that loads aggregate cells into an encapsulation device for implanting into a patient. The loading system uses negative pressure from a low pressure pump in a closed system to improve safety and cell viability while allowing for even loading of the encapsulation device.

17 Claims, 12 Drawing Sheets

(56) References Cited

U.S. PATENT DOCUMENTS

| | | |
|---|---|---|
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | D'Amour |
| 7,737,253 B2 | 6/2010 | Robins et al. |
| 8,008,075 B2 | 8/2011 | Green et al. |
| 8,129,182 B2 | 3/2012 | D'Amour et al. |
| 8,153,429 B2 | 4/2012 | Robins et al. |
| 8,211,699 B2 | 7/2012 | Robbins et al. |
| 8,216,836 B2 | 7/2012 | D'Amour et al. |
| 8,338,170 B2 | 12/2012 | Kelly et al. |
| 2002/0044495 A1* | 4/2002 | Friedman ............ B01F 11/0022 366/212 |
| 2002/0049426 A1* | 4/2002 | Butler et al. ................ 604/892.1 |
| 2002/0081724 A1 | 6/2002 | Carpenter et al. |
| 2004/0072343 A1 | 4/2004 | Verma et al. |
| 2005/0266554 A1 | 12/2005 | D'Amour et al. |
| 2007/0026515 A1* | 2/2007 | Newman et al. .......... 435/289.1 |
| 2007/0122905 A1 | 5/2007 | D'Amour et al. |
| 2009/0004238 A1 | 1/2009 | Scharp et al. |
| 2009/0011502 A1 | 1/2009 | D'Amour et al. |
| 2009/0042287 A1 | 2/2009 | D'Amour et al. |
| 2009/0081296 A1 | 3/2009 | Humes et al. |
| 2009/0104696 A1 | 4/2009 | Robins et al. |
| 2009/0220959 A1 | 9/2009 | D'Amour et al. |
| 2009/0253202 A1 | 10/2009 | D'Amour et al. |
| 2009/0298178 A1 | 12/2009 | D'Amour et al. |
| 2010/0041150 A1 | 2/2010 | Kelly et al. |
| 2010/0124564 A1 | 5/2010 | Martinson et al. |
| 2010/0151568 A1 | 6/2010 | D'Amour |
| 2010/0260728 A1 | 10/2010 | Martinson et al. |
| 2010/0279399 A1 | 11/2010 | Robins et al. |

FOREIGN PATENT DOCUMENTS

| | | |
|---|---|---|
| WO | 2010129294 A3 | 11/2010 |
| WO | 2012115619 | 8/2012 |

* cited by examiner

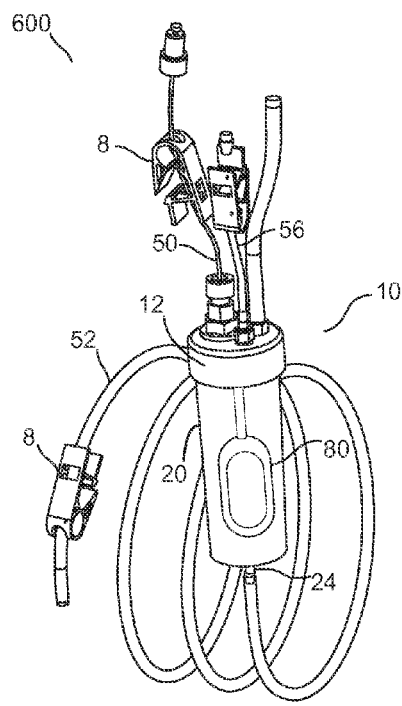
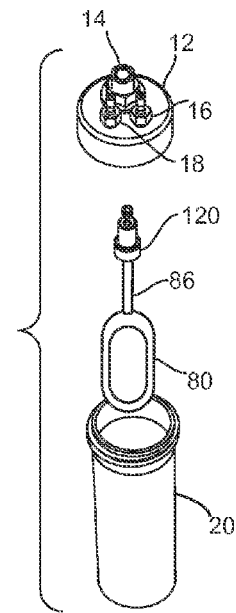
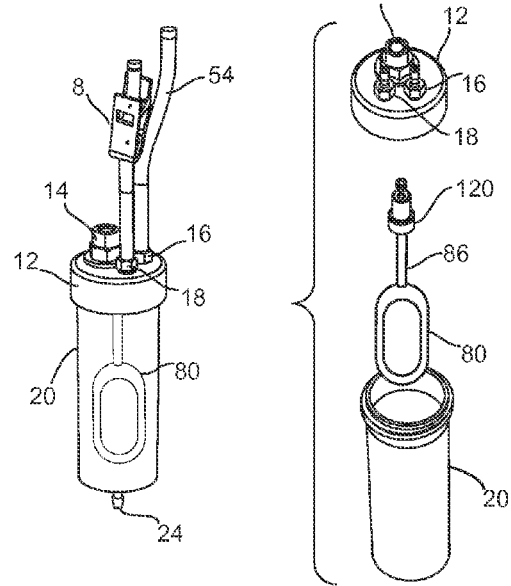
FIG. 10　　　FIG. 11　　　FIG. 12
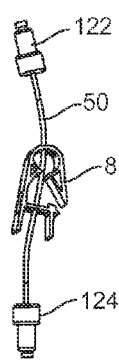
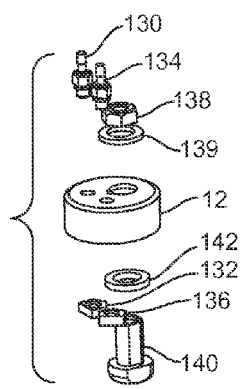
FIG. 13　　　FIG. 14

LOADING SYSTEM FOR AN ENCAPSULATION DEVICE

STATEMENT OF GOVERNMENT SUPPORT

This research was made possible by an award from the California Institute for Regenerative Medicine (Award No. DR1-01423). The contents of this publication are solely the responsibility of the inventors and do not necessarily represent the official views of CIRM or any other agency of the state of California.

RELATED APPLICATIONS

This application is a U.S. National Phase under 35 U.S.C. §371 of PCT/US11/25628, filed Feb. 21, 2011, the entire disclosure of which is incorporated herein by reference.

BACKGROUND OF THE INVENTION

1. Field of Invention

The present invention relates generally to cellular therapy and cell encapsulation, and more specifically, to techniques for loading a patient implantable encapsulation device with biological material such as, but not limited to insulin producing pancreatic cells developed from allogeneic pluripotent human stem cells, such as embryonic stem (hES) cells for the treatment of diabetes mellitus.

2. Description of Related Art

Nearly 25 million people in the United States are afflicted with diabetes mellitus, which is a disease caused by the loss of the ability to transport glucose into the cells of the body, because of either a lack of insulin production (commonly known as "Type 1" diabetes, insulin-dependent diabetes, or juvenile diabetes) or diminished insulin response (commonly known as "Type 2" diabetes). Type 1 diabetes is characterized by high blood sugar from loss of insulin producing pancreatic beta cells, leading to insulin deficiency and poor blood sugar regulation. Type 1 diabetes can result in serious complications if left untreated, such as cardiovascular disease, retinal damage, and even death. Type 1 diabetes usually cannot be cured, and has historically been managed with subcutaneous insulin injections from a syringe or an insulin pump. However, multiple daily injections of insulin do not adequately mimic the body's minute-to-minute production of insulin and precise control of glucose metabolism. Mortality and morbidity still occur today with insulin treatment from over dosage of insulin, which results in extreme hypoglycemia (low blood sugar) and coma followed by death unless reversed by someone who can quickly administer glucose to the patient. Extreme under dosage of insulin, leading to hyperglycemia (high blood sugar) and ketoacidosis can also result in coma and death if not properly and urgently treated. Even with insulin therapy, the average life expectancy of a diabetic is 15-20 years less than a healthy person.

Type 2 diabetes usually appears in middle age or later, and particularly affects those who are overweight. Over the past few years, however, the incidence of Type 2 diabetes in young adults has increased dramatically. In Type 2 diabetes, cells that normally respond to insulin lose their hormone sensitivity and fail to respond to insulin normally. This insulin resistance may be overcome for many years by extra insulin production by the pancreatic beta cells. Over time, the beta cells may become exhausted due to the burden of producing large amounts of excess insulin in response to elevated blood glucose levels. Ultimately, the overworked beta cells die and insulin secretion fails, bringing with it a concomitant rise in blood glucose to sufficient levels that it can only be controlled by exogeneous insulin injections. High blood pressure and abnormal cholesterol levels usually accompany Type 2 diabetes. These conditions, together with high blood sugar, increase the risk of heart attack, stroke, and circulatory deterioration, which in the legs can necessitate amputation. Drugs to treat Type 2 diabetes include some that act to reduce glucose absorption from the gut or glucose production by the liver, others that reduce the formation of more glucose by the liver and muscle cells, and still others that stimulate the beta cells directly to produce more insulin. Nevertheless, high levels of glucose are toxic to beta cells, causing a progressive decline of function and cell death, despite pharmacological interventions. Consequently, many patients with Type 2 diabetes eventually need exogenous insulin.

Another form of diabetes is called Maturity Onset Diabetes of the Young (MODY). This form of diabetes is due to one of several genetic errors in insulin-producing cells that restrict their ability to process the glucose that enters via special glucose receptors. Beta cells in patients with MODY cannot produce insulin correctly in response to glucose, which results in hyperglycemia. The patient's treatment eventually leads to the requirement for insulin injections.

The currently available medical treatments for patients that require exogenous insulin are limited to insulin administration and transplantation of either whole pancreata or pancreatic segments.

Insulin therapy is far more prevalent than pancreas transplantation. Insulin administration is managed conventionally by a few daily or weekly blood glucose measurements and subcutaneous injections; intensively by multiple blood glucose measurements and multiple subcutaneous injections of insulin; or continuously by subcutaneous injections of insulin with a pump. Conventional insulin therapy involves the administration of one or two injections per day of intermediate-acting insulin with or without the addition of small amounts of regular insulin. Intensive insulin therapy involves multiple administrations of intermediate- or long-acting insulin throughout the day, combined with regular or short-acting insulin prior to each meal. Continuous insulin administration involves the use of a small battery-driven pump that delivers insulin subcutaneously to the abdominal wall, usually through a 27-gauge butterfly needle. This treatment modality provides continuous insulin delivery at a basal rate throughout the day and night, with increased amounts or boluses programmed prior to meals. In each of these methods, the patient is required to frequently monitor his or her blood glucose levels and, if necessary, adjust the insulin dose. However, controlling blood sugar is not simple. Despite rigorous attention to maintaining a healthy diet, exercise regimen, and scrupulous attention to proper dosing of insulin, many other factors can adversely affect a person's blood-sugar including stress, hormonal changes, periods of growth, illness, infection and fatigue. Insulin-dependent diabetes is a chronic, life threatening disease, which requires constant vigilance.

Ultimately, it is the goal of research efforts to regenerate pancreatic insulin-producing cells in the body or repopulate these cells in situ. Although that is not possible at this time, it may eventually be feasible to transplant cells that produce insulin or precursors that will differentiate into insulin producing cells. It is likely that such cells will eventually die rather than recreate the self perpetuating system of pancreatic insulin producing cell development. Thus, they will need to be replaced periodically. In addition, exogenous cell transplantation carries the risk of introducing undesirable cell populations that may be pathogenic. Of particular concern is the possibility that a patient will receive cells capable of forming tumor in the human body. Thus, transplantation of insulin-producing cells or precursors is best performed using encapsulation forms of cells. Encapsulation permits subsequent removal of cells that are no longer therapeutically effective while reducing the risk of unwanted cell growth in the body. Furthermore, encapsulation can protect the transplant from attack by the patient's own immune system, which can destroy the transplanted cells in a short time if unabated.

Encapsulation of cells for the potential of treating a number of diseases and disorders has been discussed in the literature. The concept was suggested as early as 100 years ago, but little scientific research was performed prior to the 1950's when immunologists began using cells encapsulated within membrane devices to separate implanted cells from host cells to better understand certain aspects of the immune system. Cell encapsulation technology has potential applications in many areas of medicine. For example, in addition to treatment of diabetes (Goosen et al. (1985) Biotechnology and Bioengineering, 27:146), applications include production of biologically important chemicals (Omata et al. (1979) "Transformation of Steroids by Gel-Entrapped Nacardia rhodocrous Cells in Organic Solvent" Eur. J. Appl. Microbiol. Biotechnol. 8:143-155), and evaluation of anti-human immunodeficiency virus drugs (McMahon et al. (1990) J. Nat. Cancer Inst., 82(22) 1761-1765).

There are three main types of encapsulated devices categorized by form of encapsulation: 1) macrodevices, 2) microcapsules, and 3) conformal coatings.

Macrodevices are larger devices containing membranes in the form of sheets or tubes, and usually include supporting structures. Two major types of macrodevices have been developed: a) flat sheet and b) hollow fiber.

Among the flat sheet devices, one type (Baxter, Theracyte) is made of several layers for strength and has diffusion membranes between support structures with loading ports for replacing the cells. This device form is generally most suitable for encapsulation of insulin-producing cells.

The other important macrodevice type is the hollow fiber, made by extruding thermoplastic materials into hollow fibers. These hollow fibers can be made large enough to act as blood conduits. However, due to low packing densities, the required cell mass for clinical human dose causes the length of this type of hollow to approach many meters. Therefore, this approach has largely been abandoned for treating diabetes.

The microcapsule was one of the first to devices promising potential clinical efficacy. A microcapsule's function is to protect the graft with a membrane permeable to glucose and insulin, but impermeable to components of the immune system. One of the problems associated with microcapsules is their relatively large size in combination with low packing densities of cells, especially for the treatment of diabetes. In addition, many of the molecules used to produce microcapsules may cause an inflammatory reaction or may also be reactive within the host after implantation.

The last category of cell encapsulation is conformal coating. A conformally coated cell aggregate is one that has a substantially uniform cell coating around a cell aggregate regardless of size or shape of the aggregate. This coating not only may be uniform in thickness, but it also may be uniform in the protective permselective nature of the coating that provides uniform immunoisolation. Furthermore, it may be uniform in strength and stability, thus preventing the coated material from being violated by the host's immune system.

An important aspect to the feasibility of using these various methods of encapsulating cells for implantation is the relevant size and implant site needed to obtain a physiological result. For diabetes treatment, production of 5,000 IEQ/kg-BW of insulin is required. Injecting isolated islets into the hepatic portal vein requires 2-3 ml of packed cells to achieve this therapeutic level of insulin production. A macro-device consisting of a flat sheet that is 1 islet thick (~200 µm) requires a surface area equivalent to 2 US dollar bills. A macro-device consisting of hollow fibers with a loading density of 5% would need 30 meters of fiber. Alginate microcapsules with an average diameter of 400-600 µm would need a volume of 50-170 ml.

The stringent requirements for encapsulation polymers of biocompatibility, chemical stability, immunoprotection and resistance to cellular overgrowth restrict the applicability of existing methods of encapsulating cells and other biological materials. Due to the inability of those of skill in the art to provide all the essential properties of successful cell encapsulation, none of the encapsulation technologies developed in the past have resulted in a clinical product. These properties can be broken down into the following categories:

Biocompatibility—The materials used to make an encapsulating device must not elicit a host response, which may cause a non-specific activation of the immune system by these materials alone. When considering immunoisolation, one must recognize that it is optimal if there is minimal activation of the host immune cells in response to the materials. If there is activation of the host immune cells by the materials, then the responding immune cells will surround the device and attempt to destroy it. This process may produce cytokines that will certainly diffuse through the capsule and may destroy the encapsulated cells. Most devices tested to date have failed in part from their lack of biocompatibility in the host.

Porosity—There exists an important balance between having the largest pores possible in the barrier surrounding encapsulated cells to permit nutrients, waste materials and therapeutic products to pass through, and having the smallest pore size required to both retain cells and keep elements of the immune system segregated from the encapsulated cells. The optimal cell encapsulation barrier has an exact and consistent porosity, which allows maximal cell survival and function, as well as isolation from the host immune response.

Encapsulated Cell Viability and Function—Encapsulating materials should not be cytotoxic to the encapsulated cells either during the formation of the coatings or thereafter, otherwise the number of encapsulated cells will decrease and risk falling short of a therapeutically effective dose.

Relevant Size—Many devices are of such a large size that the number of practical implantation sites in the host is limited. Furthermore, relative diffusion distance between the encapsulated cells and the host is increased with increasing device size. The most critical diffusive agent for cell survival is oxygen, which requires minimal diffusion distances because the starting partial pressure of oxygen is already low at the tissue level in the body.

Cell Retrieval or Replacement—The encapsulating device should be retrievable, refillable, or biodegradable, allowing for replacement or replenishment of the cells. Many device designs have not considered the fact that encapsulated cells have a limited lifetime in the host and require regular replacement.

Therapeutic Effect—The implant should contain sufficient numbers of functional cells to have a therapeutic effect for the disease application in the host.

Clinical Relevance—The encapsulating cell device should have a total volume or size that allows it to be implanted in the least invasive or most physiologically relevant site for function, and which has a risk/benefit ratio below that faced by the host with the current disease or disorder.

Commercial Relevance—The encapsulating cell device should be able to meet the above requirements in order for it to be produced on an ongoing basis for the long-term treatment of the disease process for which it has been designed.

All of the above factors must be taken into consideration when evaluating a specific technique, method or product for use in implantation of insulin-producing cells to alleviate the effects of diabetes.

Transplantation of human islets with immunosuppression can be performed by introducing unencapsulated islets directly via percutaneous injection between the ribs, through the liver, and into the portal vein using fluoroscopic guidance with an introduction catheter. Essentially all of the human islet transplants have been performed using this technique. A major risk of this procedure is increased portal venous pressures depending on the rate of infusion and the amount infused. Additional risk is associated with injection of islet tissues insufficiently purified, which can also lead to portal venous thrombosis. As the interventional radiologist prepares to withdraw the catheter, a bolus of gelatin is left behind to prevent hemorrhaging from the injection site. Unfortunately, several patients have had bleeding episodes following this procedure.

In addition to injecting the islets into the portal vein, a few patients have had islets injected into the body of the spleen. The spleen is more fragile than the liver so these injections have typically been performed at the time of, e.g., kidney transplantation, thus permitting splenic injection as an open procedure. Freely injecting islets into the peritoneal cavity has been performed in mice without difficulty. In using this site in larger animals or humans, it has been found that twice the number of islets is needed if injected into the peritoneal cavity than required in the portal vein implants. If any rejection or inflammatory reactions occur, then adhesions tend to form between the loops of intestine, as well as, to the omentum. This reaction can lead to additional problems long term, such as bowel obstruction. Thus, the ability to implant encapsulated islets or other insulin-producing cells into a subcutaneous site would significantly reduce the complications associated with these other procedures and modalities.

Before any type of encapsulation device is implanted in a patient, it must be carefully loaded with cells, which has been conventionally performed manually by a skilled technician. Typically, encapsulation devices are loaded directly using positive pressure from a syringe. The technician fills the syringe with cells, and then inserts the syringe's needle into an inlet port of the encapsulation device, while the encapsulation device is outside the patient. The syringe exerts positive pressure on the cells to force the cells into the encapsulation device. The encapsulation device is then sealed and is later implanted into the patient.

However, loading an encapsulation device directly from a syringe has several drawbacks in both safety and cell viability. Cells often leak from the device when the syringe is removed from the port. The syringe's needle can also pierce the wall of the encapsulation device, permitting contamination of the outside of the encapsulating device with cells during loading or after implantation in the patient. Such contamination is a safety hazard regulated by the U.S. Food and Drug Administration. Theoretically, even a single contaminating cell could expand and/or biodistribute. The syringe also creates high positive pressure in the needle, which can cause shear stress and decrease cell viability.

SUMMARY OF THE INVENTION

The present invention overcomes these and other disadvantages of the prior art by providing encapsulation device loading devices, systems and methods for loading cells into an encapsulation device that can be implanted into a patient. The loading system uses negative pressure from a low pressure pump in a closed system to ensure safety and cell viability while allowing for even loading of the encapsulation device and preventing cross contamination.

The present invention provides, in certain embodiments, a cell encapsulation loading device that includes: a) a housing including a first housing member and a second housing member, where the first housing member can be detachably coupled to the second housing member, thereby forming a hollow device chamber; b) means for detachably coupling an encapsulation device to the housing and enclosing the encapsulation device within the hollow device chamber; c) a first port disposed through the first housing member for sterilely communicating cells and fluid medium into the encapsulation device; and d) a second port adapted for receiving negative pressure.

The loading device can also include within the hollow housing chamber an encapsulation device adapted for enclosing and retaining living cells that has a sterile internal chamber which retains cells deposited therewithin and an inlet port through which cells are communicated into the internal chamber. Conveniently, the loading device can be preassembled with an encapsulation device. Typically, the encapsulation device or at least the internal cell-retaining chamber thereof, is porous, thereby permitting fluid medium, oxygen, proteins and glucose to pass through. The loading device typically includes an internal membrane and optionally an external membrane, both of which can be surrounded by a supportive external mesh.

In certain aspects of the invention, the first (cell loading) port of the loading device is adapted for sealably accepting the inlet port of the encapsulation device, which provides the means for detachably coupling the encapsulation device to the housing.

To form the intact loading device housing, which typically has a generally cylindrical shape, the first housing member and the second housing member include mated threads for coupling the first housing member (which can be a cap) to the second housing member. In certain embodiments, the cap is a single injected molded component having the first (cell loading) port disposed therethrough and optionally including a fluid filling port and an optionally filtered vent. The first port will be adapted for detachably connecting cell delivery tubing for communicating cells and fluid medium into the encapsulation device, and may include, for example, a threaded region for accepting a mated ferrule that can be connected to the cell delivery tubing.

The second (vacuum) port of the loading device may be disposed through the second housing member, which may terminate in a tapered tip and have the second port disposed at the distal end of such tapered tip. The second port is adapted for connection to vacuum tubing, through which negative pressure can be applied.

The present invention also provides, in certain embodiments, an encapsulation device loading system that includes an encapsulation loading device described herein, a cell chamber adapted for containing living cells and fluid medium, where the cell chamber is in fluid communication with the first (cell loading) port of the encapsulation loading device through cell delivery tubing; and a pump (e.g. a peristaltic pump) for applying negative pressure to the second (vacuum) port of the encapsulation loading device, where the application of negative pressure to the second port of the encapsulation loading device is sufficient to draw living cells and fluid media from the cell chamber through the inlet port and into the internal chamber of the encapsulation device.

In operation, the encapsulation device will be enclosed within the hollow device chamber.

In certain aspects, the system also includes a means for placing the cell chamber in motion sufficient to keep the cells suspended in the fluid medium during loading, which may be an orbital rotator adapted for accepting and securing the cell chamber thereto, such as with a clamp.

The system can also include an optionally vented waste container that is coupled to the pump and is in fluid communication with the second port of the encapsulation device. In certain embodiments, the system includes at least one fluid reservoir, which can be for example, a bottle, a flask, a funnel, a tube or a bag that is in fluid communication with the inlet port of the encapsulation device for dispensing sterile fluid to the encapsulation device. In certain aspects, the system includes three fluid reservoirs for receiving and serially dispensing a wetting solution (e.g., ethanol), sterile water and a fluid medium, respectively.

Throughout the system, fluid communication is provided by tubing, which can be glass tubing, rubber tubing, stainless steel tubing and plastic tubing.

In certain embodiments, the system is multiplexed by including a second encapsulation loading device, a second cell chamber, and a second pump, etc. Multiplex loading systems can include a plurality of encapsulation loading devices of various configurations as described herein. In operation, an encapsulation device is secured within each encapsulation loading device.

To facilitate loading of the encapsulation device, the loading device can be inverted during loading through the use of a pivoting device clamp, which can be motorized and automated. Thorough and even distribution of cells within the encapsulation device can be furthered by vibrating, mixing, rotating and/or centrifuging the encapsulation device or inlet port thereof during loading. Cells may also be directed into position in the encapsulation device through various mechanisms, such as a specific geometry of the device, e.g. a geometric membrane structure or an inlet port including pores to channel the cells to specific locations.

A computer including a programmable logic controller or microprocessor can be interfaced to the system for automating the process of loading an encapsulation device with cells, i.e., by controlling pumps, motors or an orbital rotators. Feedback can be provided to the computer to signal control actions through sensors, such as level sensors, strategically located within the system and in electronic communication with the computer. For example, fluid level sensor can be used to detect the level of fluid in the fluid reservoirs, the cell chambers, or the waste containers.

Certain aspects of the present invention also provide methods for loading an encapsulation device, the method comprising the steps of a) providing a loading device as described herein; b) coupling the first port of the loading device to a cell chamber containing living cells and a fluid medium; and c) applying negative pressure to the second port to draw the living cells and the fluid medium into the encapsulation device, thereby loading the encapsulation device. Once filled, the loaded encapsulation device can be sealed for transport and implantation.

In certain embodiments and for certain types of encapsulation devices, the method requires pre-wetting, rinsing and equilibrating the encapsulation device with fluid media. This can be accomplished by filling the device chamber with ethyl alcohol and then draining the device chamber to remove the ethyl alcohol; filling the device chamber with water and then draining the device chamber to remove the water; and finally, filling the device chamber with media and draining the device chamber to remove the media. The device so processed is then ready for loading. Any encapsulation device can be used, but will typically be sufficiently porous to allow the fluid medium, oxygen, insulin, and glucose to pass through, but not living cells.

Advantageously, the methods of the invention can be semi-automated, for example, by interfacing a computer that includes a programmable logic controller or a microprocessor and which can control pumps, motors or orbital rotators of the system.

Embodiments of the present invention have several advantages over existing technology. For example, the low pressure pump eliminates cross contamination by providing a closed sterile system that does not require introduction of a syringe needle into a port, thereby preventing perforating of the encapsulation device, which can leak and potential piercing of the encapsulation device. Further, the absence of a syringe also eliminates high pressure and hydrodynamic focusing that could create situations of very high shear. Combined with the low flow, low pressure pump used, the system promotes cell viability, which is critical for sensitive cell populations such as embryonic stem cell derivatives and many other viable human or animal cells. For example, sufficient shear stresses can disrupt cell membranes, and thereby kill living cells. Moreover, in some embodiments of the invention, small cell aggregates may be loaded. It may be desirable to prevent disruption of the aggregates in such situations as unaggregated cells may be more prone to uncontrolled differentiation. Even a minimal amount of shear stress could disrupt cell aggregates to single cell suspensions. Cell viability is critical in order to minimize the number of cells that need to be loaded into the device to achieve a therapeutic dose. Reliable and reproducible dosing requires that cells loaded into the device remain viable and functional.

Further, the system can be semi-automated, significantly reducing human error that leads to cross contamination and the potential for irregular application of high pressure, while reliably distributing the cells (i.e., evenly loading) throughout the encapsulation device. The system is also adaptable to different configurations of encapsulation devices.

The foregoing, and other features and advantages of the invention will be apparent from the following, more particular description of the preferred embodiments of the invention, the accompanying drawings, and the claims.

BRIEF DESCRIPTION OF THE DRAWINGS

For a more complete understanding of the present invention, and the advantages thereof, reference is now made to the ensuing descriptions taken in connection with the accompanying drawings briefly described as follows:

FIGS. 10-14 illustrate an encapsulation loading device system according to an alternative embodiment of the invention;

DETAILED DESCRIPTION OF EMBODIMENTS

Figure 1:
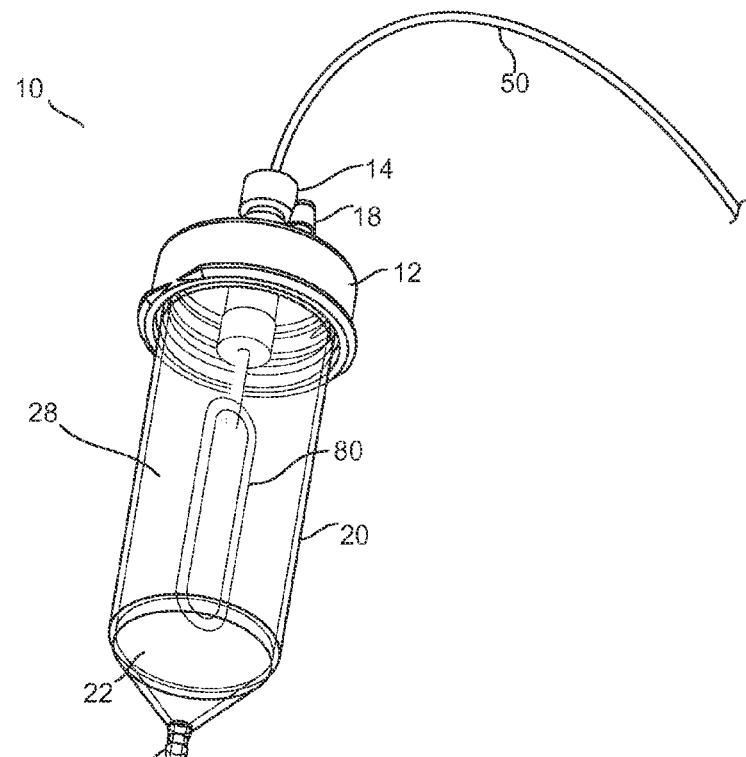
FIG. 1 illustrates an encapsulation loading device according to an embodiment of the invention.

Further features and advantages of the invention, as well as the structure and operation of various embodiments of the invention, are described in detail below with reference to the accompanying FIGS. 1-22, wherein like reference numerals refer to like elements. Although embodiments of the invention are described in the context of loading an encapsulation device with insulin producing cells for the treatment of diabetes mellitus, one of ordinary skill in the art readily appreciates that the present invention is applicable to loading an encapsulation device with any type of living cells or mixtures thereof, including but not limited to hepatic cells, endocrine cells, skin cells, hematopoietic cells, bone marrow stem cells, renal cells, muscle cells, neural cells, stem cells, embryonic stem cells, lineage-restricted cells, progenitor cells, precursor cells, genetically engineered cells, tumor cells, and derivatives and combinations thereof for the treatment of one or more disease or disorder, including, but not limited to diabetes mellitus. Also contemplated are cells producing cell-based products such as antibodies, antibiotics, lymphokines and the like for therapeutic indication. One of ordinary skill in the art also appreciates that the present invention is applicable to different encapsulation device types, materials, sizes, and/or configurations.

The present invention provides, in at least several embodiments, an encapsulation loading device, loading system and methods for loading living cells into an encapsulation device for implantation into a patient or subject in order to replace critical cell-based products lost to disease or disorder. The loading system uses negative, i.e., vacuum, pressure from a low pressure pump in a closed system to improve safety and maintain cell viability while allowing for even loading of the encapsulation device and preventing cross contamination. In a preferred embodiment of the invention, the encapsulation device is loaded with human pancreatic progenitor cells or cells derived from pancreatic progenitor cells such as human insulin-producing cells from the pancreas. In other embodiments, the cells are stem cells such as pluripotent (e.g., embryonic stem cells or induced pluripotent stem cells) or adult stem cells; partially differentiated derivates of stem cells, such as lineage restricted cells, progenitor cells, precursor cells, and fully differentiated cells. Techniques for the production of insulin-producing cells and the insertion of an encapsulated device loaded with biological material into a patient are disclosed in U.S. Pat. No. 7,427,415; U.S. Pat. No. 7,695,965; U.S. Patent Application Publication No. 2009/0004238; and U.S. Patent Application Publication No. 2010/0124564, the disclosures of all of which are incorporated herein by reference in their entirety.

Figure 2:
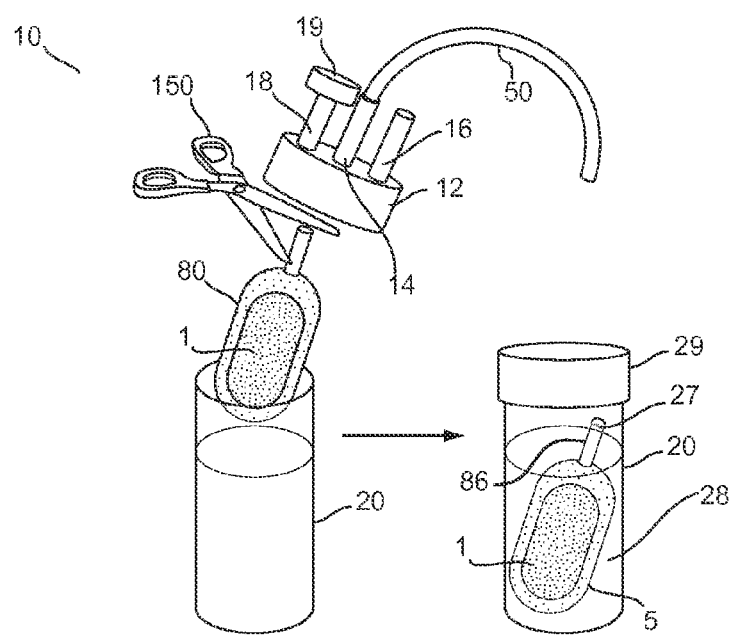
FIG. 2 illustrates an encapsulation loading device of the invention and the removal of the loaded encapsulation device therefrom according to an embodiment of the invention.

FIGS. 1 and 2 illustrate alternative, nonlimiting embodiments of the encapsulation loading device 10 according to the invention. The encapsulation loading device 10 is generally a hollow body that includes a first housing member 12 and a second housing member 20 that are adapted to be detachably connected to each other, thereby forming an encapsulation device chamber 28 in which an encapsulation device 80 can be enclosed. In the embodiment shown in FIG. 1, the second housing member 20 is represented as a modified tube having a generally cylindrical shape, while the first housing member 12 is represented as tube cap. The first housing member 12 and second housing member 20 can be configured with mated threads as shown to securely screw on to each other, forming a liquid-tight seal. Other means of detachably coupling the first and second housing members to each other will be known in the art. As used herein, "detachably coupling" refers to any means for attaching, and at least partially removing or separating one part such as the first housing member 12, from a second part such as the second housing member 20. In addition to housing members having threaded fittings, detachably coupled parts may include snap lock fittings (FIG. 2), tight pressure fittings, luer fittings, flanges and other types of connections and fittings that will be well known in the art. In certain aspects of the invention, the first housing member 12 may be completely separated from the second housing member, and for example, replaced with a sealing cap 29 for storage or transportation (as illustrated in FIG. 2). In certain aspects of the invention, detachably coupled housing members may be separated sufficiently to expose and provide access to, for example, the encapsulation device chamber 28, while still remaining tethered, bound, fastened or otherwise at least partially attached to each other. For example, the first and second housing members (12 and 20, respectively) may be connected through a hinge or swivel coupling that allows the members to remain connected to each other. Advantageously, a hinged coupling between the first and second housing members may allow the operator to open the housing to secure or remove the encapsulation device using only one hand (e.g. by snapping the cap/first housing member off of the tube/second housing member). In such aspects of the invention, the housing can be opened or closed by displacing the first housing member 12 from a fully seated, sealing position on the second housing member 20 without the need to place first housing member 12 down on a bench or other surface. Such displacement reduces the potential for contamination or accidental loss of detached parts that may accompany full separation.

When coupled together, the first and second housing members form a protected, hollow device chamber 28 in which an encapsulation device can be detachably coupled as shown in FIG. 1. In certain aspects of the invention, the filled encapsulation device 80 can also be stored in the encapsulation loading device 10 for transport, as shown in FIG. 2.

The first housing member 12 includes a cell loading port 14 for communicating cells and fluid media to an encapsulation device 80 disposed within the hollow device chamber 28. The first housing member may also include additional ports, such as a fluid filling port 16 for filling the loading device with wetting, washing and equilibration fluids prior to cell loading, and a device vent 18 (preferably equipped with a filter 19 to prevent contamination from the environment), to allow exposure to ambient air.

The second housing member includes a vacuum port 24 that is adapted for receiving negative pressure (i.e. vacuum), and may be disposed at a tapered terminal portion 22 of the second housing member 20 as illustrated in FIG. 1. Alternatively, the vacuum port 24 may be located on a side of the second housing member 20 or may even be disposed on the first housing member (not shown). Locating the vacuum port 24 on the first housing member may require additional adaptations such as tubing or the like to facilitate withdrawal of fluids from the device chamber 28, but may be advantageous when it is desirable for the encapsulation loading device 10 to rest on a bench or other surface without support.

Figure 3:
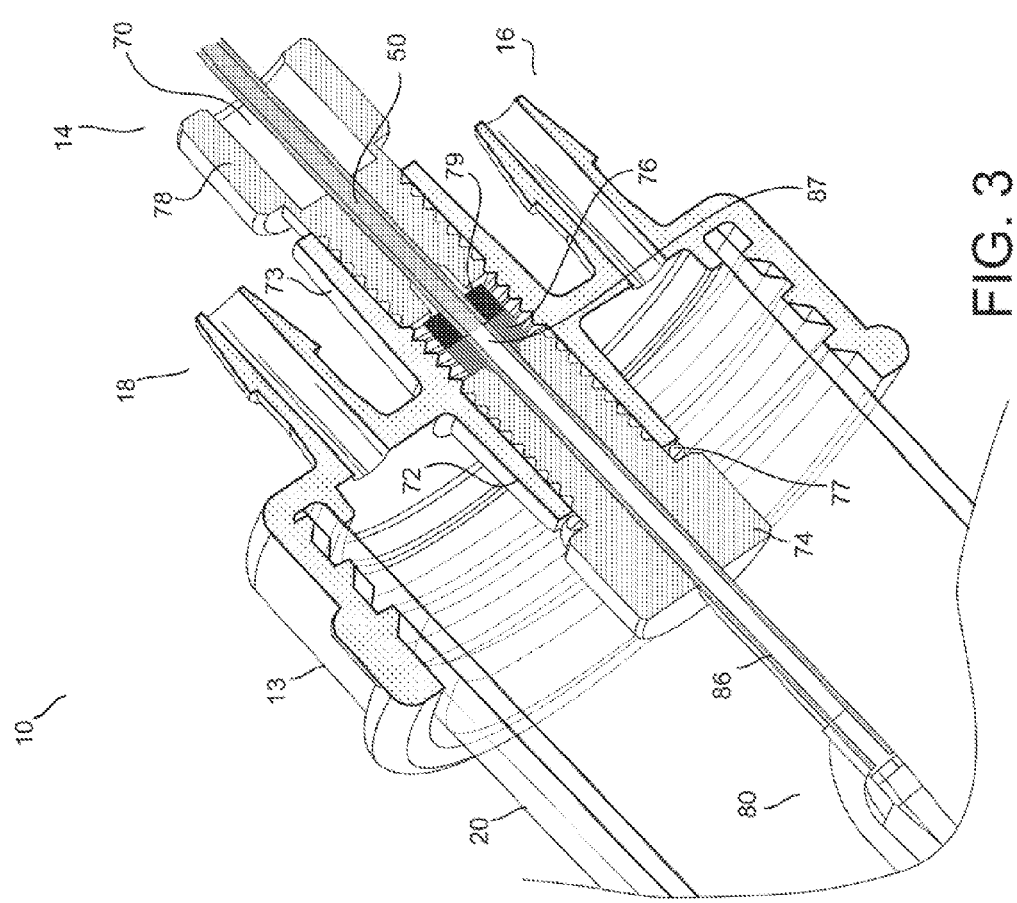
FIG. 3 illustrates a cross-sectional view of an encapsulation loading device according to an embodiment of the invention.

The first housing member 12 and the second housing member 20 may be manufactured from any suitable sterile or sterilizable material and will typically be plastic, such as a thermoplastic, thermoset or epoxy material, and may be made by any available method, including without limitation, injection molding, casting, extrusion, fabrication, machining, forming and the like. For example, the first housing member 12 can be molded, as shown in FIG. 3, as a single piece of material. In a preferred embodiment of the invention, the second housing member 20 is transparent so that a user may view the contents inside, e.g., the encapsulation device 80 as it is loaded with cells 1. However, alternative materials, shapes, and connection means may be used for the first housing member 12 and the second housing member 20, the identification and implementation of which will be apparent to one of ordinary skill in the art.

FIG. 3 illustrates a cross-sectional view of an encapsulation loading device 10 as shown in FIG. 1, where the first housing member (12) is a specially molded cap 13. Here, one can better see how the encapsulation device 80 is detachably coupled to the cap 13. In this embodiment of the invention, cap 13 includes cell loading port 14, which includes a cylindrical opening 70 traversing through cap 13. The cylindrical opening 70 includes an inner compression region 72 and outer compression region 73 extending outwardly from the respective bottom and top sides of the cap 13. The inner compression region 72 includes threads on its inner surface for receiving an oppositely threaded male adapter 74 coupled to the inlet port 86 of an encapsulation device 80. In an embodiment of the invention, the male adapter 74 has an opening traversing its axis for receiving the inlet port 86 of the encapsulation device 80. The encapsulation device 80 is coupled to the male adapter 74 by inserting the inlet port 86 through this opening where a ferrule 76 is affixed to the distal end 87 of the inlet port 86, as shown. The ferrule 76 secures the encapsulation device 80 to male adapter 74, which can be handled using aseptic technique in order to screw the male adapter 74 into the compression region 72, thereby securing the encapsulation device 80 to the cap 13. An optional O-ring 77 may be provided between the male adapter 74 and the inner compression region 72 in order to better seal the fluid pathway into the encapsulation device 80.

The outer compression region 73 includes threads on its inner surface for receiving an oppositely threaded male tubing adapter 78 coupled to cell delivery tubing 50. In certain aspects of the invention, the male tubing adapter 78 has an opening traversing its axis for receiving the cell delivery tubing 50. The cell delivery tubing is coupled to the male adapter 78 by inserting the cell delivery tubing 50 through opening 70 where a ferrule 79 is affixed to an end of the cell delivery tubing 50 as shown. The ferule 79 secures the cell delivery tubing 50 to the male adapter 78, which can be handled using aseptic technique in order to screw the male adapter 78 into the opening 70, thereby securing the cell delivery tubing 50 to the cap 13. With both male adapters 74 and 78 secured to the cap 13, the ferrules 76 and 79 abut each other, thereby forming a closed fluid passageway between the cell delivery tubing 50 and the encapsulation device inlet port 86.

Device vent 18 and fluid filling port 16, which may be disposed on cap 13, provide for the transmission of additional fluids in and out of the encapsulation loading device 10.

Figure 4:
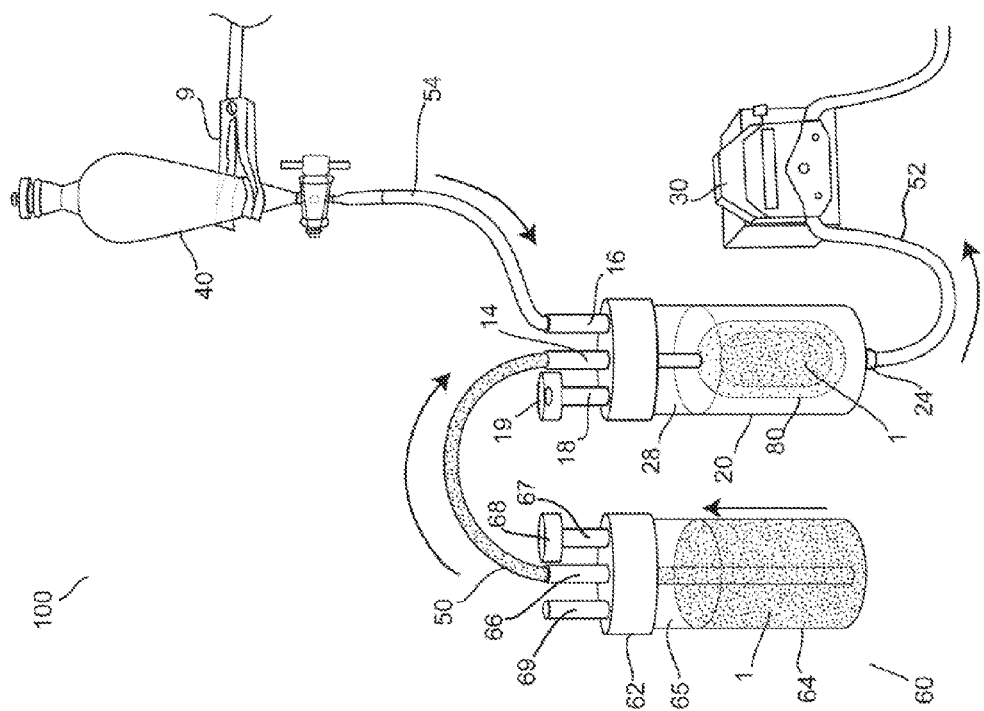
FIG. 4 illustrates an encapsulation loading system according to an embodiment of the invention.

In operation, a vacuum or negative pressure is placed on the encapsulation loading device 10 by connecting a pump to port 22 through vacuum tubing 52. Once a vacuum or negative pressure is established, cells 1 are withdrawn from a remote cell holding vessel 60 as shown in FIG. 4, through cell delivery tubing 50 connected to cell outlet port 66, which is disposed on the cell holding vessel 60. The cells are thus delivered into the encapsulation device 80 through the encapsulation device inlet port 86. To facilitate flow of the cells to the encapsulation loading device 10, the cell holding vessel 60 may include a vent 67, and optionally vent filter 68. Additional ports 69 may also be present on cell holding vessel 60 to allow addition or removal of cells and/or media (e.g., for filling, sampling or washing).

When the cells 1 are adequately transferred, the device inlet port 86 can be cut (e.g. using scissors 150) and closed (e.g., by creating a seal 27 by melting the tubing via heat treating) as shown in FIG. 2, thereby sealing the cells 1 within the encapsulation device 80 in a completely sterile manner. The loaded encapsulation device 80 is then packaged and transferred to a suitable site, e.g., a hospital, where it is removed (in a sterile environment) and implanted into a patient. Conveniently, as illustrated in FIG. 2, the loading device 10 can be used as a storage and transfer vessel by capping or sealing the ports (not shown) and/or sealably replacing the first housing member 12 with a sterile cap 29.

In certain embodiments of the invention, the encapsulation device 80 is a retrievable, durable, non-biodegradable, clinical grade, vascularizing device that enables cells 1 loaded therewithin to survive and/or differentiate into functioning insulin-producing cells. The encapsulation device 80 is manufactured from U.S. Food and Drug Administration compliant implant grade materials, the identification and implementation of which is apparent to one of ordinary skill in the art, and is designed with a goal of creating a barrier between the encapsulated cells and the patient's immune system, thereby eliminating the need for continuous administration of immunosuppressant drugs. In certain aspects of the invention, the encapsulation device 80 is optimized for cells 1 that secrete (e.g., release) insulin, after implantation and cell maturation, in response to the patient's blood glucose level and is designed for subcutaneous implantation providing complete containment of the cells 1 with full retrieval capability. Insulin is produced by the cells 1 within the encapsulation device 80 without insulin injections, immunosuppression, hypoglycemia, or other diabetes-related complications.

Figure 5:
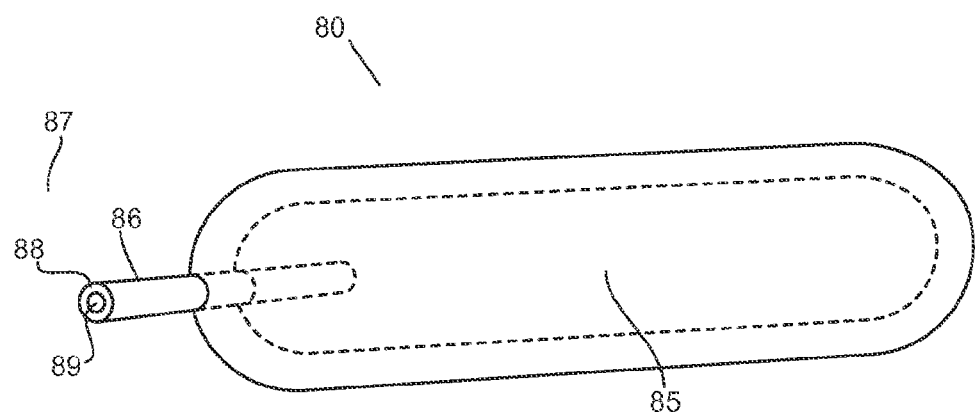
FIG. 5 illustrates an encapsulation device according to an embodiment of the invention.

FIG. 5 illustrates an exemplary encapsulation device 80 that can be loaded using the devices and systems of the invention. In this Figure, the encapsulation device 80 is illustrated as a pouch 81 for containing cells and having disposed at one end an inlet port 86 consisting of an outer tube 88 surrounding and thereby forming a hollow inner lumen 89 that has a generally tubular shape.

The pouch portion of the encapsulation device 80 will generally include at least one contiguous membrane that is selectively permeable to small molecules, insulin, nutrients and cellular waste products, but will not permit passage of cells. The membrane can be selected by the skilled artisan to have the desired molecular exclusion properties. The exemplary encapsulation device 80 shown in cross-section in FIG. 6 includes an inner membrane 83, an outer membrane 82 and a supporting exterior mesh 84. The exterior mesh 84 provides support and protection to the inner and outer membranes, 83 and 82 respectively, while permitting fluid to pass through. In one embodiment, the exterior mesh 84 comprises woven polyester mesh giving the encapsulation device 80 stiffness and stabilizing its shape. The outer membrane 82 has a porous structure that does not impede transport of oxygen, nutrients, or insulin.

Inner membrane 83 surrounds an internal chamber 85 and thereby acts as a pouch for retaining living cells within the body of a subject. The inner membrane 83 has a porous structure that does not impede transport of oxygen, nutrients, or insulin, but does prevent cells of the host immune system from contacting and destroying the cells 1. In one embodiment of the invention, the inner membrane 83 and/or outer membrane 82 comprises polytetrafluoroethylene (i.e., PTFE or "Teflon"). PTFE is a hydrophobic material such that high pressure is required to force aqueous media across prior to wetting of the membrane by a solvent. Accordingly, PTFE membranes must be wetted before aqueous liquids will pass through at low pressures. In other embodiments, the membranes 82 and 83 are pre-wetted or may be made of other materials that will not require wetting.

The encapsulation device inlet port 86 is located on one end of the encapsulation device 80 and permits the flow of cells 1 and fluid media into the device 80 from a distal, open end (87) into the internal chamber 85 of the encapsulation device. The inlet port 86 is illustrated as a single port, although certain embodiments of the present invention may include multiple ports for better flow into the encapsulation device 80. In an embodiment of the invention, the inlet port 86 includes a plastic (e.g. thermoplastic, thermoset, epoxy, etc.) structure or tube 88 surrounding a hollow, typically tubular lumen 89 through which cells and fluids are delivered.

Various types of encapsulation devices 80, each having different shapes and sizes, can be employed. The encapsulation loading device 10 and loading system 100 can adapt to (i.e., accommodate) these different shapes and sizes. In one embodiment, the encapsulation device 80 is a flattened, elliptical sheet that is sealed around the perimeter like a bag or pouch.

Figure 7:
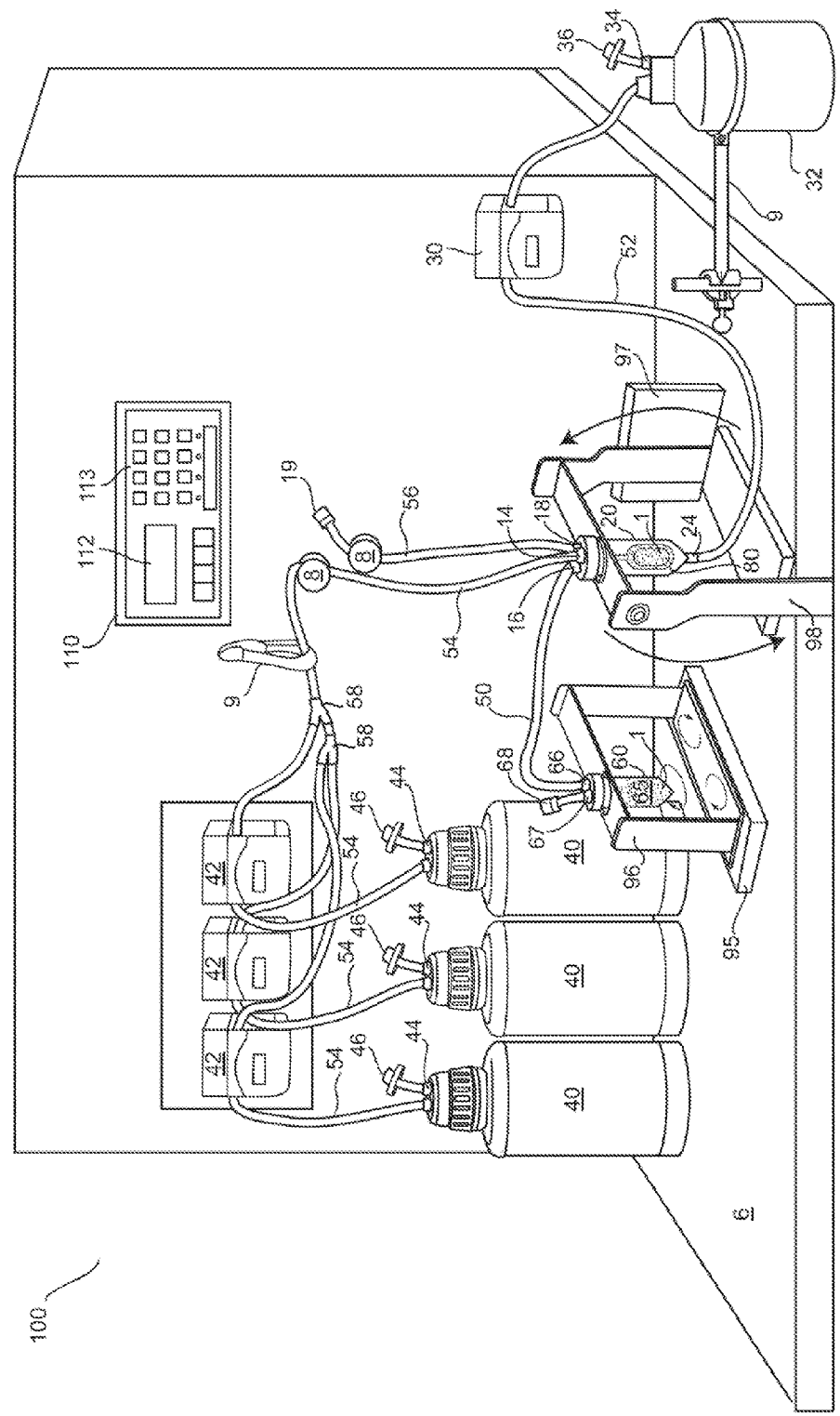
FIG. 7 illustrates an encapsulation loading device system according to an alternative embodiment of the invention.

The encapsulation loading device 10 and encapsulation device 80 are used together with other components of a loading system 100 provided by the invention. Illustrated in FIG. 4 is a basic embodiment of the encapsulation device loading system 100. Another embodiment of the encapsulation device loading system 100 is shown in FIG. 7, which includes advanced features of the systems of the invention. The skilled artisan will appreciate that basic features of the loading system are shown in FIG. 4, while the advanced features shown in FIG. 7 can be used to provide additional functionality, automation, standardization and optimization under certain conditions. The embodiment of the encapsulation device loading system 100 shown in FIG. 4 includes: a cell holding vessel 60 adapted for receiving, retaining, and dispensing cells 1, which is generally a closed, substantially hollow housing for cells and may be formed by sealably connecting a first housing member 62 to a second housing member 64 thereby forming cell chamber 65; an encapsulation loading device 10 that includes a housing comprising first and second housing members (12 and 20, respectively) enclosing a hollow device chamber 28, which is adapted for holding an encapsulation device 80, and includes a device chamber vent 18 (shown with optional filter 19), a cell loading port 14 for communicating cells and fluid media through cell delivery tubing 50 to the encapsulation device; a vacuum port 24 for receiving negative pressure, e.g. from encapsulation pump 30 through vacuum tubing 52; and a fluid filling port 16 for delivering various fluids when required (e.g. for wetting the membranes of encapsulation device 80); a waste container 32 having a waste container vent 34 with optional filter 36; suitable tubing connectors 58 as required; and one or more fluid reservoirs 40 with reservoir vents 44 and optionally, vent filters 46, for delivering fluids to the loading device through fluid tubing 54. Optionally, as desired, the system also includes a stand 6 having one or more holding clamp(s) 9 for securing various components of the loading system 100. Also included in certain loading systems 100 according to the invention (see e.g. FIG. 7) is a means for maintaining the cells in suspension during loading, such as an orbital rotator 95; and an inverting holding rack/clamp assembly 98 for tilting and inverting the encapsulation loading device 10 during loading. Optionally, the inverting holding rack/clamp assembly 98 may be coupled to a motor 97 for automating inversion of the cell loading device. In operation of the loading system 100, cells 1 are drawn from the cell chamber 65 of the cell holding vessel 60 into the encapsulation device 80.

The cell holding vessel 60 and encapsulation loading device 10 can each be any type of storage vessel and can be configured in various sizes and shapes for storing and/or receiving live cells in an enclosed, aseptic manner, i.e., preventing interaction between the cells and outside environment. The encapsulation device 80 may be of any size, shape, or type, e.g., barrier device, implantable pouch, or pancreatic progenitor pouch, provided it fits within the device chamber 28 of encapsulation loading device 10. In practice, the encapsulation device chamber 28 will be sized and shaped to accommodate the required encapsulation device 80, while the cell chamber 65 of cell holding vessel 60 will be sized and shaped to accommodate and dispense a therapeutic number of cells into the encapsulation device 80. Because the cells must be suspended in a liquid medium prior to and during loading, the cell chamber 65 will accommodate a volume that is at least 10 times the capacity of the encapsulation device 80. Typically, the volume held by of the cell holding vessel 60 will be at least 25 times, frequently at least 50 times, and often 100 or more times the capacity of the encapsulation device 80.

The waste container 32 and fluid reservoir(s) 40 can each independently be any type of liquid-holding vessel and can be configured in various sizes and shapes. All materials used in the construction of the devices and systems described herein, and particularly those that will come into contact with cells or with fluids that will contact cells, should be sterile, biocompatible and generally inert. Vessels, tubing and other device components are conveniently manufactured and packaged as disposable single-use components. However, in certain embodiments it is contemplated that one or more component of the devices and systems of the invention can be reusable. Waste containers, for example, may be reused if they are isolated from other components, or cleaned and sterilized prior to reuse to prevent contamination of critical components. Additional components such as pumps, computers, stands, clamps and rotators that do not directly contact cells or fluids can be isolated from sterile components by suitable sterile enclosures, coverings or barriers. For example, computer displays and interfaces can be concealed behind transparent sterile barriers with non-sterile portions separated from the sterile field of operation, such as by locating the equipment outside of (e.g. behind) a sterile chamber where loading is performed. Pumps and other devices or parts thereof that are contained within the sterile field can be cleaned and contact-sterilized with a suitable disinfectant or, when feasible, by irradiation, or heat, or steam sterilization (i.e. autoclaving), as will be known in the art. Suitable materials for components of the devices and systems of the invention include, but are not limited to, glass, stainless steel, plastic (thermoplastic, thermoset, epoxy, etc.), and the like. It should be noted that plastics should be of a type and grade suitable for use in preparing therapeutics for administration to human patients, and should be non-toxic and pyrogen-free. In particular, plastics that contain or leach impurities such as bisphenol A should be avoided. Suitable plastics are known in the art and widely used in pharmaceutical and surgical fields, for example for manufacturing bags, fitting and tubing for administration of intravenous fluids. Typically, components are manufactured from USP Class VI materials that enable their use in human clinical applications.

Advantageously, the encapsulation device loading system 100 can be designed to fit within a sterile cabinet, such as laminar flow cabinet or hood, thereby allowing operation in a sterile environment. In other embodiments, the cell holding vessel 60 is adapted for removal to a sterile environment, such as a laminar flow hood, for receiving cells, followed by replacement in line in the cell loading system. In yet other embodiments, the system is portable, which allows locating the system or a portion thereof, in a sterile environment, such as within or adjacent to a surgical suite or hospital type operating room. Conveniently, such operation of the system permits direct transfer of the loaded encapsulation device to the hands of surgical staff for direct implantation without packaging and transport.

In conventional encapsulation device loading systems, a syringe is filled with cells, and the syringe is used to transfer the cells (i.e., by injection using positive pressure) into an encapsulation device through an opening. In such a manual process, the syringe needle may accidentally pierce or damage the walls of the encapsulation device when inserting the needle into the opening or when loading an inner chamber of the encapsulation device, thereby causing contamination by allowing the cells to escape or be deposited on the outside of the encapsulation device and/or introducing microbial contamination into the encapsulation device. Contamination of an outside surface of the encapsulation device with cells can also occur when a syringe is withdrawn from the encapsulation device after loading. The encapsulation device loading techniques of the present invention eliminate the use of needles to load the encapsulation device 80, thereby promoting safety by preventing contamination.

Cells 1 that may be encapsulated using the devices, systems and methods of the invention can include any type of human or animal cells that may be of therapeutic benefit to a subject upon implantation. In addition to allogeneic and xenogeneic cells, autologous cells or derivatives thereof are also contemplated for use in the methods of the present invention. For example, it may be desirable to obtain stem cells or somatic cells from the subject and derive a therapeutic cell population from those cells. Such a process would reduce the risk of an immune response to the implanted cells. Exemplary cell types suitable for use in the devices, systems and methods of the invention include aggregated or single cell suspensions of human embryonic stem cells or derivatives thereof, pancreatic progenitor cells, glucose responsive beta cells, insulin producing cells, definitive endoderm cells, islet cells, tumor cells, or any combination thereof. In one embodiment of the invention, the cells 1 are generated by differentiation of human embryonic stem cells (e.g., human pluripotent stem cells) into definitive endoderm, a gatekeeper cell type that differentiates into pancreatic, hepatic and other cells, tissues and organs. Definitive endoderm can be differentiated in vitro into pancreatic progenitors cells that will produce insulin in vivo, for treating insulin-dependent Type 1 and Type 2 diabetics. See e.g., U.S. patent application Ser. No. 12/758,734 (filed Apr. 12, 2010); Ser. No. 12/710,300 (filed Feb. 22, 2010); Ser. No. 12/582,600 (filed Oct. 20, 2009); Ser. No. 12/476,570 (filed Jun. 2, 2009); Ser. No. 12/414,482 (filed Mar. 30, 2009); Ser. No. 12/167,227 (filed Jul. 2, 2008; now U.S. Pat. No. 7,534,608); Ser. No. 12/132,437 (filed Jun. 3, 2008); Ser. No. 12/107,020 (filed Apr. 21, 2008); Ser. No. 12/093,590 (filed Jul. 21, 2008); Ser. No. 12/039,701 (filed Feb. 28, 2008); Ser. No. 11/860,494 (filed Sep. 24, 2007; now U.S. Pat. No. 7,695,963); Ser. No. 11/773,944 (filed Jul. 5, 2007; now U.S. Pat. No. 7,695,965); Ser. No. 11/681,687 (filed Mar. 2, 2007); Ser. No. 11/588,693 (filed Oct. 27, 2006); Ser. No. 11/587,735 (filed Aug. 29, 2008); Ser. No. 11/165,305 (filed Jun. 23, 2005; now U.S. Pat. No. 7,541,185); Ser. No. 11/317,387 (filed Dec. 22, 2005; now U.S. Pat. No. 7,625,753); Ser. No. 11/021,618 (filed Dec. 23, 2004; now U.S. Pat. No. 7,510,876); Ser. No. 11/115,868 (filed Apr. 26, 2005); and Ser. No. 10/584,338 (filed Jan. 9, 2007; now U.S. Pat. No. 7,704,738), the contents of which are incorporated herein by reference in their entirety. In an embodiment of the invention, the cells 1 are suspended in a suitable fluid medium, such as a growth or differentiation medium, the identification and implementation of which is apparent to one of ordinary skill in the art, comprising a physiologically acceptable aqueous solution for the growth or sustained health and well-being of the living cells 1. For example, the fluid medium may comprise glucose, salts, minerals, buffers, amino acids, hormones and growth factors that the cells 1 need and use in vitro and/or in vivo. Exemplary fluid media contemplated for use in the present invention are described in U.S. patent application Ser. No. 10/486,408 (now U.S. Pat. No. 7,432,104); Ser. Nos. 10/416,361; 11/678,487; 11/838,054; 11/764,752; 12/604,942; 11/875,057; 12/264,760 and PCT International Application No. PCT/US10/32601, the contents of which are incorporated by reference herein in their entirety.

The encapsulation loading device 10 is fluidly connected to the cell holding vessel 60 with cell delivery tubing 50 as shown, which improves safety by providing a closed, sterile pathway for the cells 1 from the cell holding vessel 60 to the encapsulation device 80, as well as enclosure and protection of the encapsulation device 80 during loading. The closed pathway and enclosures eliminate the chances of cross contamination by keeping the exterior of the encapsulation device 80 clean and aseptic, reducing potential microbial contamination risk, and protecting the device from sharp objects, such as a syringe needle. Moreover, the external surface of the encapsulation device 80 is physically separated from other surfaces, including tubing that is in contact with the cell holding vessel 60, such that contamination of the exterior of the encapsulation device 80 with the cells 1 is virtually impossible. The device chamber vent 18, which can be a filtered vent, sterile filtered vent, closable vent, etc. when fitted with optional filter 19, permits optional ambient air flow to facilitate movement of fluids and cells within the closed system.

The encapsulation pump 30 is connected to the vacuum port 24 of encapsulation loading device 10 by vacuum tubing 52 as shown and described above and promotes safety by being adjustable, reliable, and reproducible, which reduces human error associated with conventional syringe-based loading systems that create high pressure through manual application of force. High pressure may cause leaks which contaminate the outside of the encapsulation device 80, and may create shear forces that damage or kill cells. Conventional loading systems rely on manual and/or positive pressure to load the encapsulation device 80, which can be quite high in magnitude through small bore-hole syringe needles. As a result, loading by this approach has been inconsistent, uncontrolled, uneven, and subject to cell product loss due to the extremely high pressures that are generated (e.g., greater than 10 psi). High pressure is created when the injection force is distributed over the small cross sectional area of the syringe bore. As pressure is equivalent to the ratio of applied force over the area in which the force is applied, the result in small internal diameter syringes and needles is elevated pressure.

In contrast, encapsulation pump 30 generates a relatively low vacuum pressure, (i.e., negative pressure) which is applied to the encapsulation loading device 10 to thereby draw the cells 1 from the cell holding vessel 60 into the encapsulation device 80. Most of the fluid medium or culture liquid in which the cells 1 in the cell holding vessel 60 are suspended is drawn through the porous surface of the encapsulation device 80 and removed as waste, while the cells 1 are retained in the encapsulation device 80. The resulting low pressure is due to the distribution of the force over the entire porous surfaces of the encapsulation device 80 rather than the internal diameter of a syringe. The loading system 100 generates less than 2 psi in pressure, typically less than 1 psi pressure and often less than 0.5 psi is required to operate the system. This low pressure maintains cell viability and eliminates leaks by gently transferring the cells 1 into the encapsulation device 80. The encapsulation pump 30 allows for precise control of the loading flow rate and allows for a low and controllable negative pressure (i.e., a low vacuum pressure). The encapsulation pump 30 can be any type of pump, the identification and implementation of which is apparent to one of ordinary skill in the art, including, but not limited a peristaltic pump, a low pressure pump, a negative pressure pump, a vacuum pump, a fluid pump, a mechanical pump, an automated pump, a variable speed pump, a reversible pump, and combinations thereof. In one exemplary embodiment, the pump is a variable speed, reversible, peristaltic pump with an input configured to couple size 14 tubing.

Waste container 32 is connected to the encapsulation pump 30 through vacuum tubing 52, which drains fluid from the encapsulation loading device 10 as needed. Waste container vent 34, which may be a filtered vent, sterile filtered vent, closable vent, etc. when fitted with optional filter 36, provides the option of ambient air flow. Tubing connector(s) 58 are used as needed to complete the system, as illustrated connecting three fluid reservoirs 40 to a single port on the encapsulation loading device 10 via fluid tubing 54. Before loading, the connector 58 connects the fluid reservoirs 40 to the encapsulation loading device 10. In one embodiment, the connector 58 is a three gang four-way stopcock manifold.

The fluid reservoirs 40 allow for dispensing fluids to wet and clean the encapsulation loading device 10, and to prepare the encapsulation device 80 for loading (e.g., wetting membranes of encapsulation device 80). In one embodiment, one of fluid reservoirs 40 contains ethyl alcohol (EtOH) for wetting the encapsulation device 80, a second fluid reservoir 40 contains water for rinsing the ethyl alcohol from the encapsulation device to avoid precipitation of substances that may clog membranes, and a third fluid reservoir 40 contains suitable media for holding and/or sustaining living cells 1. In certain embodiments where wetting the encapsulation device 80 is not required, a single fluid reservoir 40 containing media for equilibrating the encapsulation device 80 can be used. In one embodiment, the fluid reservoirs 40 are 250 mL separatory funnels as shown in FIG. 4, that may have stopcock vents for better flow. In other embodiments, the reservoirs are bottles, flasks, carboys or bags such as i.v. bags, or the like. The reservoir vents 44 (e.g., filtered vent, sterile filtered vent, closable vent, etc.) give the option for ambient air flow while maintaining a sterile environment.

In certain aspects of the invention, the fluid reservoirs 40 are filled with calibrated volumes of fluid required for wetting, washing, rinsing etc. In these aspects, the entire amount of fluid in the reservoir is dispensed and the order of fluid delivery can be controlled, for example, by selectively operating the corresponding reservoir pump 42. In other aspects of the invention, the reservoirs are filled with an excess amount of fluid and delivery can be controlled by selectively operating both the corresponding reservoir pump 42 and pinch valve 8, which stop flow of a particular fluid type once the required amount has been delivered. Fluid level or flow sensors strategically located at various points in the system, such as on the fluid reservoirs 40, fluid tubing 54, waste container 32, vacuum tubing 52, cell holding vessel 60, cell delivery tubing 50, encapsulation device 80, etc., can be used to monitor the amount of fluid dispensed and/or delivered through the system.

The optional stand 6 may include holding clamps 9 to provide support for various components of the loading system 100. One of ordinary skill in the art appreciates that the stand 6 may be replaced with any type of fixture that secures the various components of the loading system 100 relative to one another. In certain aspects, stand 6 holds the encapsulation pump 30 and waste container 32, and gives the loading system 100 more portability. In yet further embodiments, stand 6 is a cabinet or hood structure that further protects the system and its individual components from contamination.

One or more holding clamps 9 mounted to the stand can be used to secure the encapsulation loading device 10 and/or the various components of the loading system 100. The skilled artisan will appreciate that holding clamps 9 can be integrated into the stand 6 or the stand 6 can be customized to accept individual components of the system. In certain aspects of the invention, a specialized rack/clamp assembly 98 is used that includes a pivoting arm to adjust the angle of the encapsulation loading device 10. In a preferred embodiment, the encapsulation loading device 10 is inverted (i.e., the connector side turned toward the ground) during loading. In another embodiment, the encapsulation loading device 10 is adjusted to a horizontal position during loading. In yet another embodiment, the position of the encapsulation loading device 10 is changed during loading, such as a stepped change or continuous change in position. It is well within the level of the skill in the art to determine the optimal position of the encapsulation loading device 10 to maximize the desired distribution of cells in the encapsulation device 80.

In one embodiment of the invention, the cell holding vessel 60 is vibrated, rotated, stirred or shaken during loading to prevent the cells 1 from settling out of the media, which would lead to uneven or incomplete loading, as well as to prevent the cells 1 from sticking together excessively. As illustrated in FIG. 7, this can be accomplished by placing the cell holding vessel 60 on an orbital rotator 95 or similar device fitted with a rack/clamp assembly 96 which holds the cell chamber 60 to the platform of the rotator.

Figure 8:
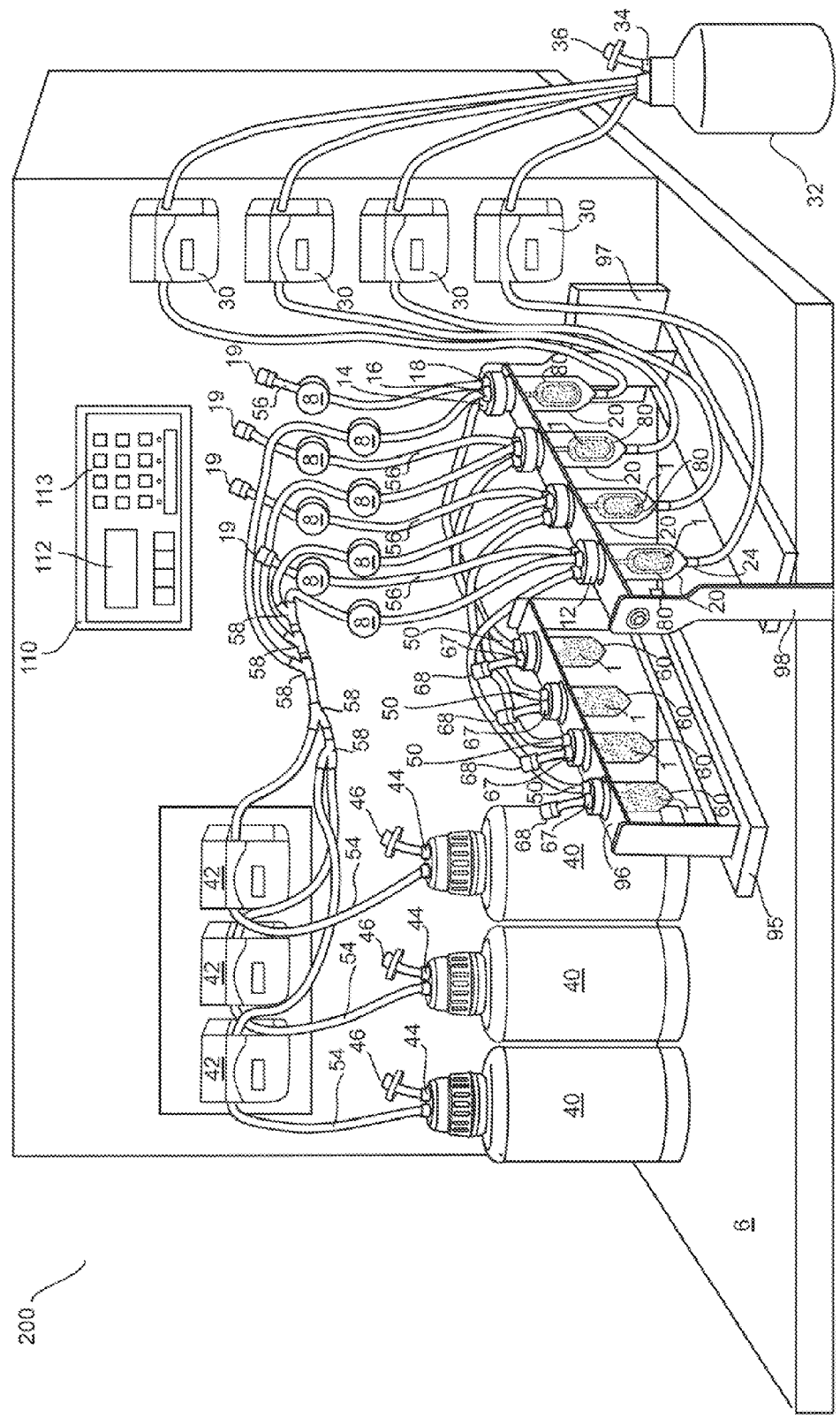
FIG. 8 illustrates a multiplexed encapsulation device loading system according to an embodiment of the invention.
Figure 9:
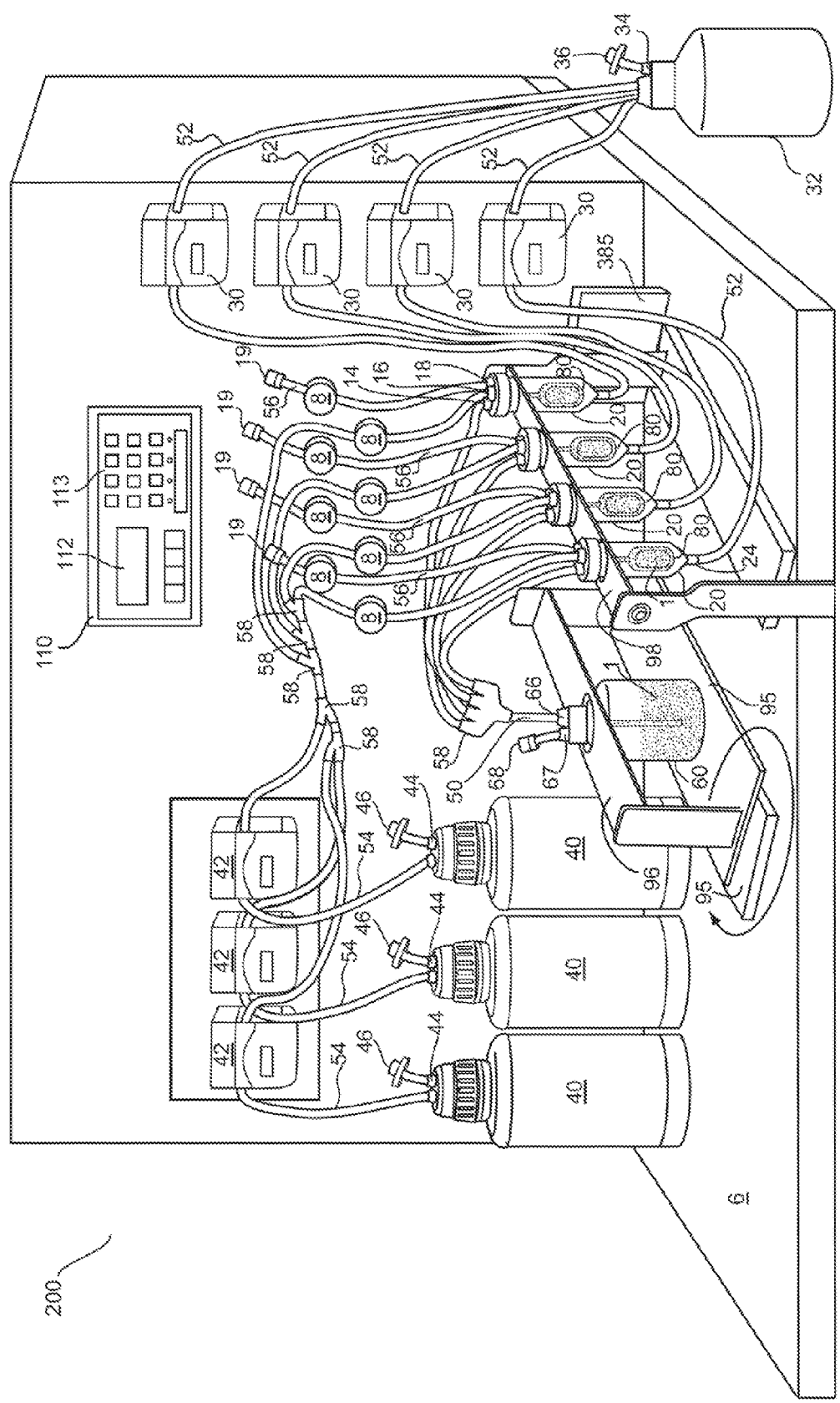
FIG. 9 illustrates an alternative multiplexed encapsulation device loading system according to an embodiment of the invention.

FIGS. 8 and 9 illustrate multiplexed encapsulation device loading system 200 according to various embodiments of the invention. The multiplexed encapsulation device loading systems 200 allow sequential or parallel loading of multiple or a plurality of encapsulation loading devices 10, which can be performed in a semi-automated fashion. The multiplexed encapsulation device loading system 200 shown in FIG. 8 includes a plurality of cell holding vessels 60 for receiving, retaining, and dispensing cells 1, and a mated set of encapsulation loading devices 10, each including loading ports 14, fluid filling ports 16, vacuum ports 24, device chamber vents 18, optional device chamber vent filters 19, and having disposed therewithin one or more encapsulation devices 80. As shown, the vacuum port 24 of each encapsulation loading device 10 is fluidly connected to an encapsulation pump 30, which in turn empty into a common waste container 32. The skilled artisan will appreciate that individual waste containers 32 can also be provided for each encapsulation loading device 10 if it is necessary to isolate the waste media from each device loaded. Fluid reservoirs 40 having fluid reservoir vents 44 supply pre-loading fluids, such as wetting solution, water and media, respectively, via fluid tubing 54 coupled to mated reservoir pumps 42, through a common connector 58, which in turn distributes the fluids to each of the plurality of encapsulation loading devices 10 via the fluid tubing 54. In the embodiments illustrated, a stand 6 having a specialized inverting rack/clamp 98, supports the encapsulation loading devices 10, which may be inverted to facilitate loading. Optionally, a computer 110 comprising a programmable logic controller or a microprocessor, and having a display 112 and a keypad 113 can be used to monitor and/or facilitate automation of device loading. As shown, the display 112 and keypad 113 may in a position facing the encapsulation loading device(s) 10 so that the operator can observe and react to both output from the computer and visual cues from the loading operation. Alternatively, the display 112 and keypad 113, along with other component of the system 200 may be separated from the encapsulation loading device(s) 10, by the stand or another partition to eliminate the possibility of contamination by the operator.

The exemplary multiplexed encapsulation device loading system 200 illustrated in FIG. 8 loads cells 1 from four cell holding vessels 60 into four encapsulation devices 80. In an embodiment of the invention, the cell holding vessel 60 and encapsulation loading devices 10 may be substantially the same form factor, but only the encapsulation loading devices 10 include an encapsulation device 80 installed therein. The illustrated multiplexed encapsulation device loading system 200 can load a plurality of encapsulation devices 80 faster than the single chamber loading system 100. In another embodiment, the multiplex chamber loading system 200 loads more or less than four encapsulation loading devices 10 at a time (e.g., 2, 3, 5, 6, 7, 8, etc.). In yet further embodiments, the multiplexed encapsulation device loading system 200 permits loading multiple cell types into a single encapsulation device 80 (not shown) or a different cell type into each of a plurality of encapsulation devices.

An alternative embodiment of the multiplexed encapsulation device loading system 200 of the invention is shown in FIG. 9. Here, a single large cell holding vessel 60 secured to a large orbital rotator 95 is used to deliver the same type of cells to a plurality of encapsulation devices 80. Individual encapsulation devices 80 can be loaded sequentially or simultaneously. In yet another embodiment of the invention, multiplexed encapsulation device loading system 200 includes an orbital rotator 95 and rotator rack/clamp assembly 96 with interchangeable modules for accepting one, two or a plurality of cell holding vessel 60 sized according to the number of encapsulation devices 80 that are to be filled.

The encapsulation device loading system 100 and multiplexed encapsulation device loading system 200 can be semi-automated, where a computer 110 with a microprocessor or programmable logic controller is interfaced with the system to allow programmable automation, while keypad 113 and display 112 allow for manual input, which may by prompted by the computer 110 or by visual inspection of the loading system. In various embodiments, the computer 110 is in electronic communication with and can control any or all of: the encapsulation pumps 30, the reservoir pumps 42, the orbital rotator 95 for rotating the cell holding vessel 60, the motor 97 coupled to rack/clamp assembly 98 holding the encapsulation loading devices 10 for inverting the encapsulation loading devices 10 during cell loading, pinch valves 8 that regulate fluid flow from the fluid reservoirs 40, liquid level sensors (not shown) and the device chamber vents 18. Feedback during loading operations can be provided by strategically located sensors such as liquid level sensors (not shown) that monitor the fluid reservoirs 40, cell holding vessel(s) 60 and encapsulation loading devices 10. Such sensor may operate on any known mechanism for detecting fluid levels, including but not limited to impedance. For example, a fluid reservoir liquid level sensor can be included to detect when a sufficient volume of wetting solution has been delivered from the fluid reservoir 40 to the encapsulation device 80 and instruct the reservoir pumps 42 and/or pinch valve 8 to cease delivery of wetting solution and begin delivery of water. Also contemplated for optional inclusion in an automated encapsulation device loading system of the invention are other types of sensors, such as Coulter counter-type sensors, which can measure the delivery of cells 1 to the encapsulation device(s) 80 to standardize loading of a therapeutic number of cells to each encapsulation device loaded in a single loading or in loadings performed at different times. Various types of sensors that may be incorporated into the system and in electronically connected to computer 110 will be well known to the skilled artisan.

The encapsulation pumps 30 can be connected to the computer 110 with programmable logic controller or microprocessor for automation of negative pressure. The encapsulation pumps 30 are connected to the encapsulation loading devices 10 by vacuum tubing 52 as shown, and promote safety by being adjustable, reliable, and reproducible, which reduces human error associated with conventional syringe-based loading systems that can create high pressure through manual application of force. In contrast, the encapsulation pumps 30 generate a relatively low vacuum pressure, i.e., negative pressure, which is applied to the encapsulation loading devices 10 to thereby draw the cells 1 from the cell holding vessel 60 into the encapsulation devices 80.

The reservoir pumps 42 may be in electronic communication with computer 110 having programmable logic controller or microprocessor, for automation of fluid delivery, and allow for washing of the cell holding vessel 60 and encapsulation loading devices 10 and preparing the encapsulation devices 80 for loading with little intervention. In one embodiment, one of reservoirs fluid reservoirs 40 contains ethyl alcohol (EtOH) for wetting the encapsulation devices 80, one of fluid reservoirs 40 contains water for cleaning the ethyl alcohol off the encapsulation devices 80 to avoid precipitate clogging membranes and to prevent contact between the cells and the ethyl alcohol, and one of reservoirs 40 contains a medium that promotes cell 1 survival. The connector 58 is illustrated as connecting three reservoirs 40 to the encapsulation loading devices 10.

The stand 6 having holding clamps 9 provides support for the multiplexed encapsulation device loading system 200. The stand 6 holds the encapsulation pumps 30, the waste containers 32 (shown in FIG. 7), the reservoir pumps 42, and the computer/programmable logic controller 110, and gives the multiplexed encapsulation device loading system 200 more stability and portability. The rotator holding rack/clamp assembly 96 holds the cell holding vessel 60, and is connected to the computer/programmable logic controller 110 for automated control of the movement of the cell holding vessel 60. In some aspects, a specialized, pivoting inversion holding rack/clamp assembly 98, also connected to computer 110, can adjust the orientation of the encapsulation loading devices 10 in response to a user pressing buttons on the keypad 113 or as an automated step built into the computer/programmable logic controller 110. In one embodiment, the encapsulation loading devices 10 are adjusted to be upside down (i.e., the inlet side towards the ground) during at least a part of the loading.

The remaining components of the multiple chamber loading system 200 (e.g., cell holding vessel 60 adapted for receiving, retaining, and dispensing cells 1, encapsulation loading devices 10 having device chamber vents 18 and encapsulation devices 80, waste containers 32 having waste container vents 34 with optional filter 36, and a connector 58 can function like the components described above, but in a sequentially loaded, semi-automated, multiplexed fashion. For example, the encapsulation/vacuum pumps 30 can be operated sequentially (one at a time) to load a first encapsulation device 80 until a sufficient number of cells has been loaded, which can be determined e.g. visually, by fluid level sensor-determined volume delivered to the encapsulation device 80, or by Coulter-type counter sensor feedback signalling a therapeutic dose of cells loaded. Thereafter, the first encapsulation pump 30 is turned off and loading of the second encapsulation device 80 proceeds by turning on the second encapsulation pump 30.

The cell holding vessel 60 and encapsulation loading devices 10 can be any type of storage vessel in various sizes and shapes for storing and/or receiving live cells in an enclosed manner, i.e., preventing interaction between the cells and outside atmosphere. The encapsulation devices 80 may be of any size, shape, or type, e.g., barrier device, implantable pouch, or pancreatic progenitor pouch, so long as they fit within the encapsulation loading devices 10. The invention further contemplates that multiple encapsulation devices 80 may be held in a single encapsulation loading device 10 for simultaneous loading in certain embodiments. The fluid reservoirs 40 and waste containers 32 can be any type of storage vessel configured in various sizes and shapes. The multiplexed encapsulation device loading system 200 eliminates the need for needles to load the encapsulation devices 80, enables sequential loading of 1, 2, 3, 4, 5, 6, 7, 8, 9, 10 or any number of encapsulation devices 80, is gentle and promotes cell viability by utilizing low vacuum pressure for loading and promotes safety by being closed thereby preventing cross contamination.

In certain embodiments of the invention, the cell holding vessel 60, encapsulation loading devices 10, tubing and other part that may contact cells are manufactured as sterile disposable, single use items. In other embodiments, one or more of such items are provided in a washable and sterilizable form. In yet further embodiments of the invention, the encapsulation loading devices 10 may be provided preassembled with encapsulation devices disposed therein. For example, sterile, single use encapsulation loading device assemblies may be manufactured and packaged for use in the devices, systems and methods of the invention as described herein. Optionally, such assemblies also include individually wrapped caps 29 that can be positioned over the openings of the encapsulation loading device after the encapsulation device is filled, and thereby obviate the need for removal of the encapsulation device for transportation. Such assemblies reduce handling of the encapsulation device until it is ready to be implanted into the patient.

The illustrated waste containers 32 are fluidly connected to the fluid reservoir 40. In another embodiment, the waste containers 32 are also fluidly connected to the encapsulation pumps 30. The device chamber vents 18, the waste container vents 34, and the reservoir vents 44, each with optional filter, give the option for ambient air flow. The encapsulation devices 80 are discussed further with respect to FIGS. 1 and 3 above.

FIG. 1 illustrates the encapsulation device 80 according to an embodiment of the invention. FIG. 3 is a cross-sectional view of the device shown in FIG. 1. In this embodiment, the encapsulation device 80 comprises an outer membrane 82, an inner membrane 83 and an inlet port 86 (see FIG. 6). When a vacuum or negative pressure is applied across the membranes, the inlet port 86 receives cells 1 from the cell holding vessel 60. The fluid medium accompanying the cells 1 is drawn through the outer and inner membranes (82 and 83, respectively) leaving behind the cells 1 within the internal chamber 85 of encapsulation device 80. The cells 1 cannot pass through the inner membrane 83.

Figure 6:
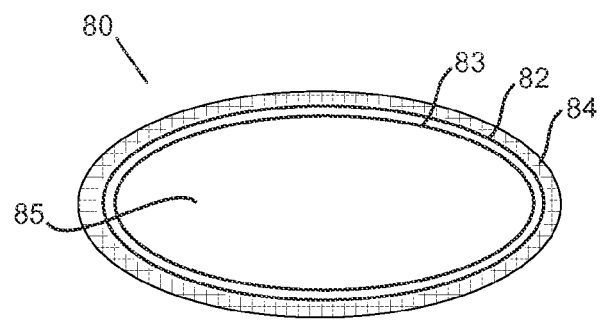
FIG. 6 illustrates a cross-section of the encapsulation device shown in FIG. 5.

FIG. 6 shows the encapsulation device of FIGS. 1-5 in cross section. As shown, the device is generally a double-layer membrane sack having an outer membrane 82, an inner membrane 83 surrounding an internal chamber 85, and an exterior mesh 84 for support. Disposed at one end of the device is an inlet port 86, which is a generally rigid, tubular structure defining a hollow lumen 89 through which cells are communicated to the internal chamber 85. In certain embodiments, the encapsulation device 80 includes only a single membrane and optionally, a supporting architecture, such as exterior mesh 84.

FIGS. 10-14 illustrate aspects of an encapsulation device loading system 600 according to an alternative embodiment of the invention. FIG. 10 illustrates an encapsulation loading device 10 coupled to tubing, including vacuum tubing 52, fluid tubing 54 and cell delivery tubing 50. The encapsulation loading device 10 comprises a cylindrical housing member 20 (second housing member) where one end culminates in a vacuum port 24. The other end is configured to receive a first housing member 12, which in this embodiment is a cap. The cap 12 is secured to the cylindrical second housing member 20 via mated threads disposed on each housing member. The vacuum port 24 is coupled to vacuum tubing 52, which may be coupled to a pump to drain fluids such as water, ethyl alcohol and media, from the encapsulation device into a fluid container (i.e. a waste container).

FIG. 11 illustrates the cap 12 shown in FIG. 10 in greater detail. The cap 12 comprises three ports 14, 16, and 18. The device loading port 14 serves as a transmission path for cells 1 into the encapsulation device 80 via cell chamber connection tubing 50. Ports 16 and 18 are for transmission of various fluids into the encapsulation loading device 10, and venting of vacuum pressure, respectively, via fluid tubing 54 and vent tubing 56. Pinch clips or valves 8, may be fastened to vacuum tubing 52, fluid delivery tubing 54 and vent tubing 56 (numbered in FIGS. 7-9 only for device vents) at one or more points along its length for stopping the flow of fluid. Pinch clips or valves 8 according to various embodiments of the invention, may be of a manually operated type as illustrated in FIGS. 10, 11 and 13, and/or may be mechanical and optionally automated (e.g. through a computerized mechanism, such as a programmable logic controller as shown in FIGS. 7-9).

FIG. 12 illustrates an exploded view of the encapsulation loading device 10 as shown in FIG. 10. The encapsulation device 80 is connected to an adapter 120 via inlet port 86. The adapter 120 is configured to connect to the bottom side (hidden from view) of the cap 12, thereby securing the encapsulation device to the encapsulation loading device 10. FIG. 13 illustrates the cell delivery tubing 50, which is coupled to the exterior surface of the cap 12 at the cell loading port 14. Here, the cell delivery tubing 50 is coupled to a device chamber adapter 124 at one end and a cell chamber adapter 122 at the other end. The device chamber adapter 124 is coupled to the cell loading port 14. The cell chamber adapter 122 is coupled to the cell holding vessel 60.

FIG. 14 illustrates an exploded view of components for connecting the device chamber adapter 124 and the inlet port 86 to the cap 12 as shown in FIG. 10. Here, a filling plug 130 connects to a filling nut 132, and a vent plug 134 connects to a vent nut 136. An aggregate nut 138 and an aggregate top washer 139 connect to an aggregate union 140 and an aggregate bottom washer 142. In one embodiment, custom injection molding is used on the connections to prevent loose or inconsistent attachments of fittings that lead to undesirable leaks and quality problems associated with manual assembly. In another embodiment, silicon grade adhesive is used to seal the connectors to prevent leaks. In another embodiment, cyanoacrylate adhesive is used. In one aspect of the invention, encapsulation device loading system 600 is custom manufactured from USP Class VI materials that enable its use in human clinical applications.

FIGS. 15-20 illustrate various alternative mechanisms that may be employed to provide even loading of the encapsulation device 80 according to other embodiments of the invention. Shown in each of FIGS. 15-20 is an encapsulation device 80 having an inlet port 86. Even loading (e.g., cell product distribution) affects the number of cells 1 that can be loaded into the encapsulation device 80 and even loading places the cells 1 in the optimal functional configuration to achieve accurate dosing of the patient and to prevent necrosis of cells 1 as a result of oxygen transport limitations that may occur in overloaded regions of the device 80. The embodiments shown in FIGS. 15-20 may be used in conjunction with negative pressure as described herein.

Figure 15:
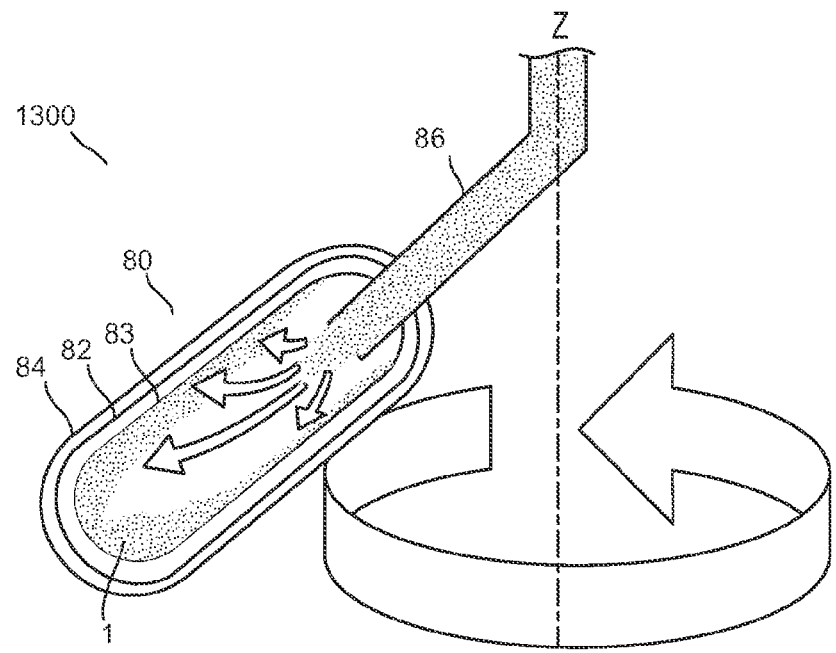
FIG. 15 illustrates a spin loading system according to an embodiment of the invention.

FIG. 15 illustrates aspects of a centrifugal loading device 1300 according to an embodiment of the invention. Particularly, a centrifugal loading device 1300 would utilize radial forces generated by rotating the encapsulation device 80 about a Z axis at relatively low angular velocity. Such a centrifugal approach may gently force the cells 1 throughout the internal chamber of the encapsulation device 80. Although the Z axis is shown as being vertical, the Z axis can include a horizontal component in a alternate embodiments.

Figure 16:
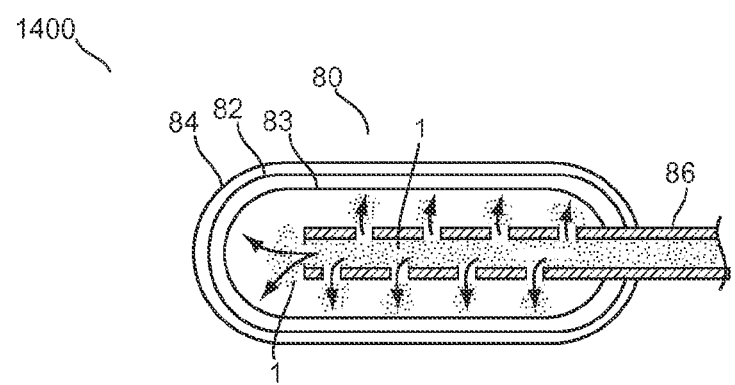
FIG. 16 illustrates an alternative encapsulation device according to an embodiment of the invention.

FIG. 16 illustrates aspects of an encapsulation loading device 1400 according to an embodiment the invention. Here, the inlet port 86 would extend into the encapsulation device 80 and include perforations or holes for directing the flow of cells within the device. The cells 1 may exit the holes to spread more evenly throughout the internal chamber of the encapsulation device 80.

Figure 17:
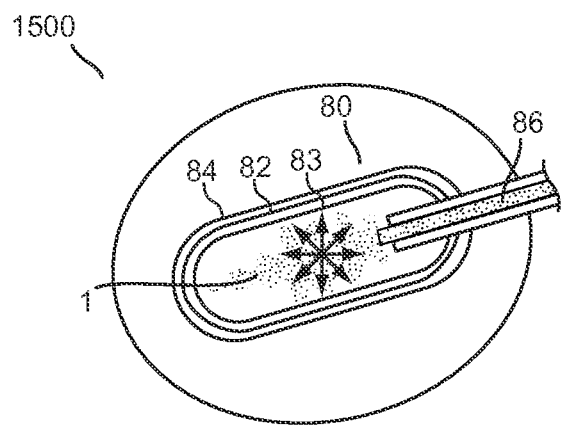
FIG. 17 illustrates an alternative encapsulation device and vibration loading system according to an embodiment of the invention.

FIG. 17 illustrates aspects of a vibrational encapsulation loading device 1500 wherein the encapsulation device 80 would be vibrated, i.e., jiggled or shaken, to spread the cells 1 evenly throughout the internal chamber of the encapsulation device 80.

Figure 18:
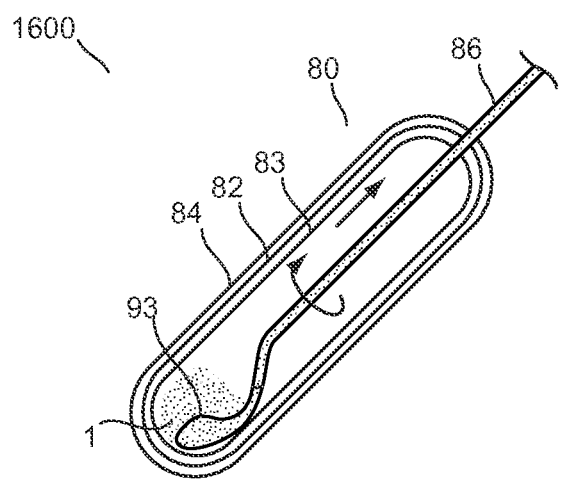
FIG. 18 illustrates an alternative encapsulation device according to an embodiment of the invention.

FIG. 18 illustrates aspects of an encapsulation loading device 1600 according to an embodiment of the invention. Here, inlet port 86 would extend into the encapsulation device and comprise a mixing end 94. The inlet port 86 and the mixing end would rotate relative to the encapsulation device 80 to spread the cells 1 throughout the encapsulation device 80. The mixing end 94 may be shaped as a spoon, paddle, or any other configuration that facilitates mixing of cells, the identification of which is apparent to one of ordinary skill in the art, to promote mixing.

Figure 19:
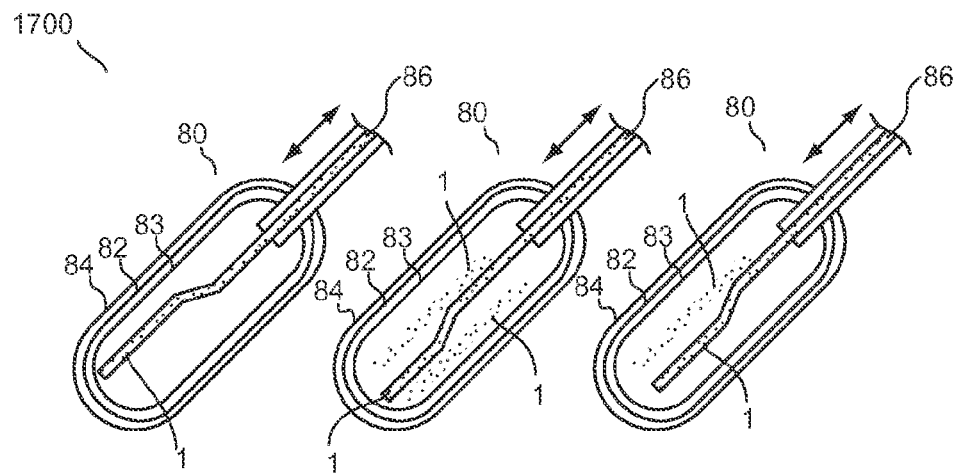
FIG. 19 illustrates an encapsulation device loading process according to an embodiment of the invention.

FIG. 19 illustrates aspects of an encapsulation loading device 1700 according to an embodiment of the invention. Here, slowly rotating the encapsulation device 80 would spread the cells 1 throughout the device in wide strokes as indicated by the bands of cells as shown.

Figure 20:
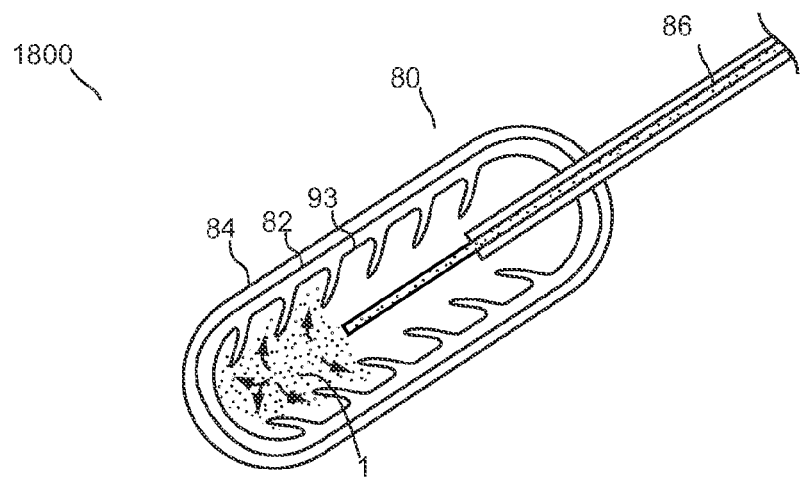
FIG. 20 illustrates a process for preparing, loading, and implanting the cells into an alternative encapsulation device according to an embodiment of the invention.

FIG. 20 illustrates aspects of an encapsulation loading device 1800 according to an embodiment of the invention. Here, the encapsulation device 80 would comprise a geometrically shaped inner membrane 93. The geometrically shaped inner chamber 93 would be constructed in such as way as to increases the surface area of inner membrane 93 to improve oxygen and nutrient transportation, and hence insulin production when loaded with cells 1.

Figure 21:
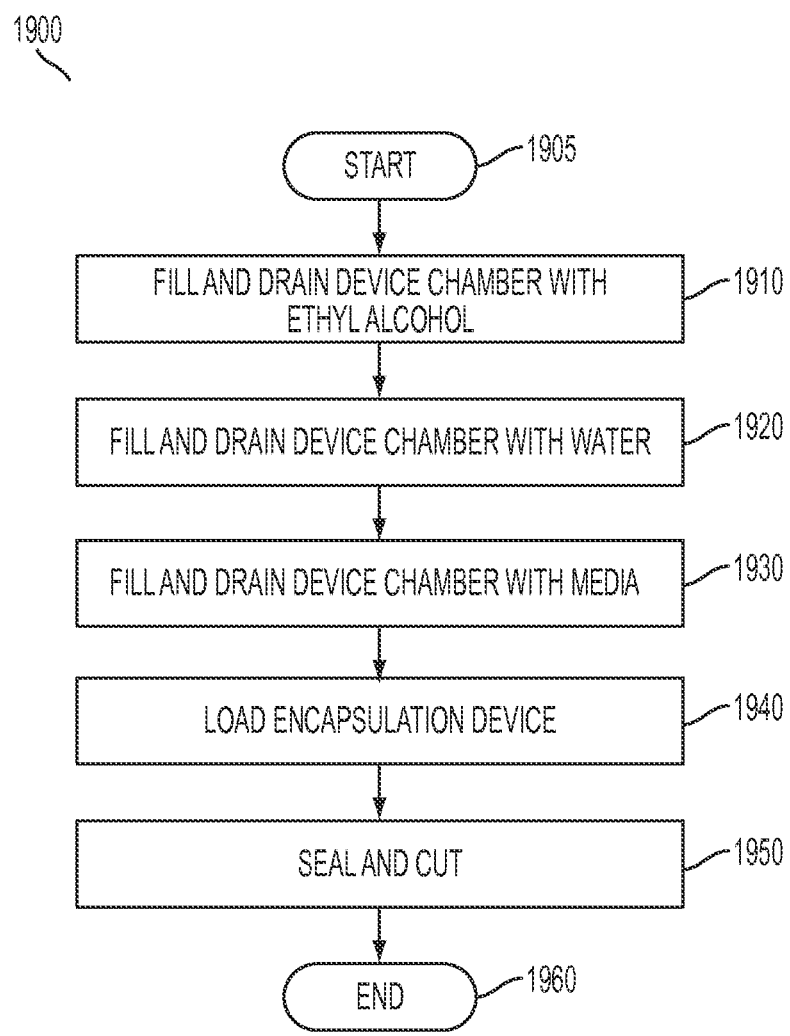
FIG. 21 is a block flow diagram of an encapsulation device loading process 1900 according to an embodiment of the invention.

FIG. 21 illustrates an encapsulation device loading process 1900 according to an embodiment of the invention. The process starts at step 1905. At step 1910, one fluid reservoir 40 supplies ethyl alcohol to wet the encapsulation device 80 inside the encapsulation loading device 10, and the pump 30 drains the ethyl alcohol. At step 1920, another fluid reservoir 40 supplies water to cleanse the encapsulation device 80, and the pump 30 drains the water. Step 1920 may be repeated as appropriate. At step 1930, another fluid reservoir 40 supplies media to equilibrate the encapsulation device 80, and the pump 30 drains the water. Next, at step 1940, the pump 30 is turned on to draw the cells 1 from the cell holding vessel 60 to the encapsulation device 80. The pump 30 can be turned off after the encapsulation device 80 is filled and pressure can be released by opening the encapsulation loading device vent 18. Continuing to step 1950, the encapsulation loading device 10 is sealed and cut. In one embodiment, the encapsulation loading device 10 is labeled and shipped to a medical provider. The process ends at step 1960.

Figure 22:
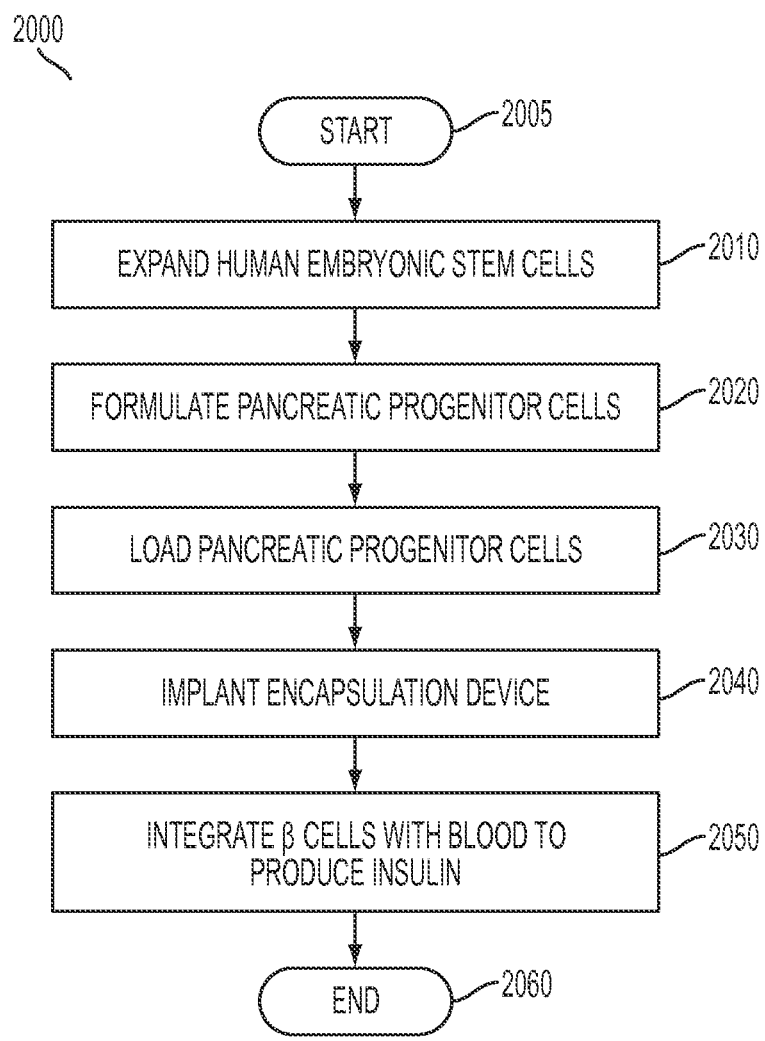
FIG. 22 is a block flow diagram of a process 2000 for preparing, loading, and implanting cells according to an embodiment of the invention.

FIG. 22 illustrates a process 2000 for preparing, loading, and implanting cells 1 according to an embodiment of the invention. The process starts at step 2005. At step 2010, human embryonic stem cells are expanded over a two-week period, and then the cell batch is differentiated in a suspension culture to become pancreatic progenitor cells over an additional two-week period. Next, the resulting pancreatic progenitor cells are frozen to allow time for safety and efficacy testing before being thawed and formulated at step 2020.

Proceeding to step 2030, the pancreatic progenitor cells are loaded into the encapsulation device 80. At step 2040, the encapsulation device 80 is grafted into the patient. Next, at step 2050, the pancreatic progenitor cells mature into glucose responsive β cells, and after the encapsulation device 80 becomes vascularized, the β cells are supplied with oxygen and nutrients while releasing insulin in response to glucose to control the subject's blood sugar. The process ends at step 2060.

It is to be recognized that depending on the embodiment, certain acts or events of any of the methods described herein can be performed in a different sequence, may be added, merged, or left out altogether (for example, not all described acts or events are necessary for the practice of the method). Moreover, in certain embodiments, acts or events may be performed concurrently, for example, through multi-threaded processing, interrupt processing, or multiple processors, rather than sequentially.

The steps of a method or algorithm described in connection with the embodiments disclosed herein may be embodied directly in a computer or electronic storage, in hardware, in a software module executed by a processor, or in a combination thereof. A software module may reside in a computer storage such as in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a mobile station. In the alternative, the processor and the storage medium may reside as discrete components in a mobile station.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

We claim:

1. A cell encapsulation loading system comprising:
   a) a cell encapsulation loading device comprising
      (1) a housing comprising a first housing member and a second housing member, wherein the first housing member is coupled to the second housing member, thereby forming a hollow device chamber and
      (2) an encapsulation device comprising an inlet port wherein the inlet port is detachably coupled to the housing and the encapsulation device is enclosed within the hollow device chamber; and
   b) an inverting holding rack for tilting or inverting the cell encapsulation loading device during loading.

2. The cell encapsulation loading system of claim 1, wherein the housing further comprises a first port.

3. The cell encapsulation loading system of claim 2, wherein the housing further comprises a second port.

4. The cell encapsulation loading system of claim 3, wherein the second port is adapted for receiving negative pressure.

5. The cell encapsulation loading device system of claim 2, wherein the first port is adapted for sterilely loading cells into the encapsulation device.

6. The cell encapsulation loading system of claim 1, wherein the encapsulation device further comprises living cells.

7. The cell encapsulation loading system of claim 1, wherein the first housing member and the second housing member are detachably coupled.

8. The cell encapsulation loading system of claim 1, further comprising:
   a cell chamber containing living cells and fluid medium, wherein the cell chamber is in fluid communication with the encapsulation loading device.

9. The cell encapsulation loading system of claim 8, wherein the living cells and fluid media are loaded into the encapsulation device through the inlet port.

10. The cell encapsulation loading system of claim 8, further comprising at least one fluid reservoir that is in fluid communication with the loading device for dispensing sterile fluid to the encapsulation device, wherein the reservoir is selected from the group consisting of a bottle, a flask, a funnel, a tube and a bag.

11. The cell encapsulation loading system of claim 8, further comprising a computer for automating a process of loading the encapsulation device with the living cells and fluid medium.

12. The cell encapsulation loading system of claim 1, wherein the inverting holding rack is coupled to a motor for automating inversion of the cell loading device.

13. The cell encapsulation loading system of claim 8, further comprising a means for maintaining the cells in suspension during loading.

14. The cell encapsulation loading system of claim 13, wherein the means for maintaining the cells in suspension during loading is an orbital rotator.

15. The cell encapsulation loading system of claim 1, further comprising a means for loading cells using negative pressure.

16. A method of loading an encapsulation device, the method comprising the steps of:
   a) providing a cell encapsulation loading system according to claim 1;
   b) providing a cell chamber comprising living cells and a fluid medium; and
   c) applying negative pressure to draw the living cells and the fluid medium through the inlet port and into the encapsulation device, thereby loading the encapsulation device.

17. The method of claim 16, wherein the method is semi-automated.

\* \* \* \* \*